US010106480B2

(12) United States Patent
Sankaranarayanapillai et al.

(10) Patent No.: US 10,106,480 B2
(45) Date of Patent: Oct. 23, 2018

(54) METHODS FOR PRODUCING FUELS, GASOLINE ADDITIVES, AND LUBRICANTS USING AMINE CATALYSTS

(71) Applicants: The Regents of the University of California, Oakland, CA (US); BP Corporation North America Inc., Houston, TX (US)

(72) Inventors: Shylesh Sankaranarayanapillai, Albany, CA (US); Sanil Sreekumar, Midland, MI (US); F. Dean Toste, Piedmont, CA (US); Alexis T. Bell, Oakland, CA (US); Amit A. Gokhale, Scotch Plains, NJ (US); Adam Grippo, Oakland, CA (US)

(73) Assignees: The Regents of the University of California, Oakland, CA (US); BP Corporation North America Inc., Houston, TX (US)

( * ) Notice: Subject to any disclaimer, the term of this patent is extended or adjusted under 35 U.S.C. 154(b) by 0 days.

(21) Appl. No.: 15/522,269

(22) PCT Filed: Oct. 28, 2015

(86) PCT No.: PCT/US2015/057901
§ 371 (c)(1),
(2) Date: Apr. 26, 2017

(87) PCT Pub. No.: WO2016/069805
PCT Pub. Date: May 6, 2016

(65) Prior Publication Data
US 2017/0334823 A1    Nov. 23, 2017

Related U.S. Application Data

(60) Provisional application No. 62/072,383, filed on Oct. 29, 2014.

(51) Int. Cl.
| | | |
|---|---|---|
| *C07C 45/71* | (2006.01) | |
| *C07C 49/00* | (2006.01) | |
| *C10L 1/00* | (2006.01) | |
| *B01J 31/02* | (2006.01) | |
| *C10L 1/02* | (2006.01) | |
| *C07C 49/04* | (2006.01) | |

(52) U.S. Cl.
CPC ........... *C07C 45/71* (2013.01); *B01J 31/0237* (2013.01); *C07C 49/04* (2013.01); *C10L 1/02* (2013.01)

(58) Field of Classification Search
CPC ............ C07C 45/71; C07C 49/04; C10L 1/02
USPC ....................................... 568/347
See application file for complete search history.

(56) References Cited

U.S. PATENT DOCUMENTS

| | | | |
|---|---|---|---|
| 2,434,631 A | 1/1948 | Winkler et al. | |
| 3,781,307 A | 12/1973 | Chabardes et al. | |
| 4,250,259 A | 2/1981 | Hou et al. | |
| 7,671,246 B2 | 3/2010 | Dumesic et al. | |
| 8,075,642 B2 | 12/2011 | Dumesic et al. | |
| 2001/0003784 A1 | 6/2001 | Kramer et al. | |
| 2005/0089979 A1 | 4/2005 | Ezeji et al. | |
| 2007/0244328 A1 | 10/2007 | Wang et al. | |
| 2007/0275447 A1 | 11/2007 | Lewis et al. | |
| 2008/0015395 A1 | 1/2008 | D'Amore et al. | |
| 2008/0015397 A1 | 1/2008 | D'Amore et al. | |
| 2008/0103337 A1 | 5/2008 | D'Amore et al. | |
| 2008/0132730 A1 | 6/2008 | Manzer et al. | |
| 2008/0244961 A1 | 10/2008 | Rusek et al. | |
| 2008/0248540 A1 | 10/2008 | Yang | |
| 2009/0030239 A1 | 1/2009 | D'Amore et al. | |
| 2009/0036716 A1 | 2/2009 | D'Amore et al. | |
| 2010/0076233 A1 | 3/2010 | Cortright et al. | |
| 2010/0077655 A1 | 4/2010 | Bauldreay et al. | |
| 2010/0204526 A1 | 8/2010 | Kouba et al. | |
| 2010/0263265 A1 | 10/2010 | Delfort et al. | |
| 2010/0268005 A1 | 10/2010 | Rusek et al. | |
| 2010/0330633 A1 | 12/2010 | Walther et al. | |
| 2011/0172475 A1 | 7/2011 | Peters et al. | |
| 2011/0237833 A1 | 9/2011 | Koltermann et al. | |
| 2011/0306801 A1 | 12/2011 | Schucker | |
| 2012/0059205 A1 | 3/2012 | Rusek | |
| 2014/0137465 A1* | 5/2014 | Toste ...................... C07C 45/71 |
| | | | 44/438 |

FOREIGN PATENT DOCUMENTS

| | | |
|---|---|---|
| CN | 101440381 A | 5/2009 |
| CN | 101787378 A | 7/2010 |
| CN | 102019177 A | 4/2011 |
| CN | 102188967 A | 9/2011 |
| CN | 102389829 A | 3/2012 |
| CN | 102600827 A | 7/2012 |
| DE | 2257675 | 5/1974 |
| EP | 0444460 A2 | 9/1991 |
| EP | 0719751 A1 | 7/1996 |
| EP | 0828558 B1 | 12/2001 |
| GB | 400384 | 10/1933 |
| GB | 723280 | 2/1955 |
| WO | 1997/19905 A1 | 6/1997 |
| WO | 1998/51813 A1 | 11/1998 |
| WO | 2007/149397 A2 | 12/2007 |

(Continued)

OTHER PUBLICATIONS

Alonso et al., "Catalytic Conversion of Biomass to Biofuels", Green Chemistry, vol. 12, 2010, pp. 1493-1513.

(Continued)

*Primary Examiner* — Sikarl A Witherspoon
(74) *Attorney, Agent, or Firm* — Morrison & Foerster LLP

(57) ABSTRACT

Provided herein are methods for producing ketone(s) from the condensation of methyl ketone(s) and alcohol(s) in the presence of an amine catalyst and a metal catalyst. Such amine catalysts may be supported, for example, on a silica-alumina support. Such ketones may be suitable for use in producing fuels, gasoline additives, and/or lubricants, or precursors thereof. The methyl ketone(s) and/or alcohol(s) may be obtained from renewable sources, such as by fermentation of biomass.

24 Claims, 7 Drawing Sheets

(56) References Cited

FOREIGN PATENT DOCUMENTS

| WO | 2008/066579 A1 | 6/2008 |
|---|---|---|
| WO | 2008/066581 A1 | 6/2008 |
| WO | 2008/109877 A1 | 9/2008 |
| WO | 2008/111941 A2 | 9/2008 |
| WO | 2008/156320 A1 | 12/2008 |
| WO | 2009/152495 A2 | 12/2009 |
| WO | 2010/098694 A2 | 9/2010 |
| WO | 2011/077242 A1 | 6/2011 |
| WO | 2011/143392 A1 | 11/2011 |
| WO | 2012/001416 A1 | 1/2012 |
| WO | 2012/001417 A1 | 1/2012 |
| WO | 2012/166267 A2 | 12/2012 |
| WO | 2012/166267 A3 | 4/2013 |
| WO | 2014/176552 A2 | 10/2014 |

OTHER PUBLICATIONS

Alonso et al., "The α-Alkylation of Methyl Ketones with Primary Alcohols Promoted by Nickel Nanoparticles under Mild and Ligand-less Conditions", Synlett, No. 12, 2007, pp. 1877-1880.

Ayame et al., "Alumina Solid Lewis Superacid: Activated Benzene and Isomerization of Alkanes on Aluminas Chlorinated at High Temperature", Journal of the Chemical Society, Chemical Communications, 1989, pp. 645-646.

Das et al., "Influence of the Metal Function in the "One-Pot" Synthesis of 4-Methyl-2-Pentanone (Methyl Isobutyl Ketone) from Acetone over Palladium Supported on Mg(Al)O Mixed Oxides Catalysts", Catalysis Letters, vol. 71, No. 3-4, 2001, pp. 181-185.

Debecker et al., "Exploring, Tuning and Exploiting the Basicity of Hydrotalcites for Applications in Heterogeneous Catalysis", Chemistry—A European Journal, vol. 15, 2009, pp. 3920-3935.

Demirbas, A. "The Importance of Bioethanol and Biodiesel from Biomass", Energy Sources, Part B, vol. 3, 2008, pp. 177-185.

Ekeley et al., "The Condensation Products of Diethyl Ketone", Journal of the American Chemical Society, vol. 46, 1924, 5 pages, pp. 446-450.

Goulas et al., "Synergistic Effects in Bimetallic Palladium—Copper Catalysts Improve Selectivity in Oxygenate Coupling Reactions", Journal of the American Chemical Society, vol. 138, 2016, pp. 6805-6812.

Hamid et al., "Borrowing Hydrogen in the Activation of Alcohols", Advanced Synthesis & Catalysis, vol. 349, 2007, pp. 1555-1575.

He et al., "One-Step Synthesis of 2-Pentanone from Ethanol over K-Pd/MnO$_x$-ZrO$_2$-ZnO catalyst", Journal of Molecular Catalysis A: Chemical, vol. 226, 2005, pp. 89-92.

Hermann, Schlenk, "Beitrag Zur Kenntnis Der Polyen-diketone", Jahrg, vol. 81, 1948, pp. 175-178. (See Communication under 37 CFR § 1.98(a) (3)).

Stetter et al., "Addition Von Aldehyden an Aktivierte Doppelbindungen, XIX. Darstellung Von Ungesattigten 1,4-Diketonen", Chemische Berichte, vol. 112, 1979, pp. 84-94. (See Communication under 37 CFR § 1.98(a) (3)).

Hong-Qing et al., "Preparation and Characterization of Amine Grafted SBA-15 Catalysts and their Application in Aldol Condensation Reaction", Chemistry and Industry of Forest Product, vol. 34, No. 2, Apr. 2014, pp. 1-8 (English Abstract Submitted).

International Preliminary Report on Patentability received for PCT Application No. PCT/US2015/022086, dated Oct. 6, 2016, 9 pages.

International Preliminary Report on Patentability received for PCT Patent Application No. PCT/US2012/035306, dated Dec. 12, 2013, 11 pages.

International Preliminary Report on Patentability received for PCT Patent Application No. PCT/US2014/040760, dated Dec. 17, 2015, 13 pages.

International Preliminary Report on Patentability received for PCT Patent Application No. PCT/US2015/057893, dated May 11, 2017, 8 pages.

International Preliminary Report on Patentability received for PCT Patent Application No. PCT/US2014/035545, dated Nov. 5, 2015, 13 pages.

International Search Report and Written Opinion received for PCT Patent Application No. PCT/US2012/035306, dated Feb. 13, 2013, 16 pages.

International Search Report and Written Opinion received for PCT Patent Application No. PCT/US2014/035545, dated Nov. 24, 2014, 18 pages.

International Search Report and Written Opinion received for PCT Patent Application No. PCT/US2014/040760, dated Nov. 25, 2014, 19 pages.

International Search Report and Written Opinion received for PCT Patent Application No. PCT/US2015/022086, dated Sep. 29, 2015, 14 pages.

International Search Report and Written Opinion received for PCT Patent Application No. PCT/US2015/057893, dated Jan. 29, 2016, 11 pages.

International Preliminary Report on Patentability received for PCT Patent Application No. PCT/US2015/057901, dated May 11, 2017, 8 pages.

Iuchi et al., "Synthesis of ω-Hydroxy Carboxylic Acids and α, ω-Dimethyl Ketones Using α, ω-Diols as Alkylating Agents", The Journal of Organic Chemistry, vol. 75, No. 5, 2010, pp. 1803-1806.

Kim et al., "Recyclable Gold Nanoparticle Catalyst for the Aerobic Alcohol Oxidation and C—C Bond Forming Reaction between Primary Alcohols and Ketones under Ambient Conditions", Tetrahedron, vol. 65, 2009, pp. 1461-1466.

Kretchmer et al., "A New Furan Synthesis", The Journal of Organic Chemistry, vol. 43, No. 24, 1978, pp. 4596-4598.

Kwon et al., "Recyclable Palladium Catalyst for Highly Selective α Alkylation of Ketones with Alcohols", Angewandte Chemie, vol. 44, 2005, pp. 6913-6915.

Margelefsky et al., "Cooperative Catalysis by Silica-Supported Organic Functional Groups", Chemical Society Reviews, vol. 37, 2008, pp. 1118-1126.

Motokura et al., "Acid-Base Bifunctional Catalysis of Silica-Alumina-Supported Organic Amines for Carbon-Carbon Bond-Forming Reactions", Chem. Eur. J., vol. 14, 2008, pp. 4017-4027.

Motokura et al., "Bifunctional Heterogeneous Catalysis of Silica-Alumina-Supported Tertiary Amines with Controlled Acid-Base Interactions for Efficient 1, 4-Addition Reactions", Chem. Eur. J., vol. 15, 2009, pp. 10871-10879.

Motokura et al., "Heterogeneous Organic Base-Catalyzed Reactions Enhanced by Acid Supports", Journal of the American Chemical Society, vol. 129, 2007, pp. 9540-9541.

Nakatsu et al., "A convenient Synthesis of Olefins via Deacylation Reaction", Tetrahedron, vol. 60, 2004, pp. 2337-2349.

Non Final Office Action Received for U.S. Appl. No. 14/786,153, dated Feb. 17, 2017, 10 pages.

Non-Final Office Action received for U.S. Appl. No. 14/123,064, dated Jan. 4, 2016, 10 pages.

Non-Final Office Action received for U.S. Appl. No. 14/123,064, dated Jan. 31, 2017, 9 pages.

Non-Final Office Action received for U.S. Appl. No. 14/123,064, dated Jul. 15, 2016, 10 pages.

Non-Final Office Action received for U.S. Appl. No. 14/895,851, dated Dec. 12, 2016, 23 pages.

Notice of Allowance received for U.S. Appl. No. 14/895,851, dated Apr. 21, 2017, 8 pages.

Patel et al., "Synthetic Talc as a Solid Base Catalyst for Condensation of Aldehydes and Ketones", Journal of Molecular Catalysis A: Chemical, vol. 286, 2008, pp. 31-40.

Qiu et al., "Synthesis and Evaluation of Curcumin Analogues as Potential Thioredoxin Reductase Inhibitors", Bioorganic & Medicinal Chemistry, vol. 16, 2008, pp. 8035-8041.

Requirement for Restriction/Election received for U.S. Appl. No. 14/786,153, dated Aug. 30, 2016, 10 pages.

Roffler at al., "Design and Mathematical Description of Differential Contactors Used in Extractive Fermentations", Biotechnology and Bioengineering, vol. 32, 1988, pp. 192-204.

(56) References Cited

OTHER PUBLICATIONS

Roffler at al., "In Situ Extractive Fermentation of Acetone and Butanol", Biotechnology and Bioengineering, vol. 31, 1988, pp. 135-143.
Roffler et al., "In-Situ Recovery of Butanol during Fermentation", Bioprocess Engineering, Part 1: Batch extractive fermentation, vol. 2, 1987, pp. 1-12.
Roffler et al., "In-Situ Recovery of Butanol during Fermentation", Bioprocess Engineering, Part 2: Fed-batch extractive fermentation, vol. 2, 1987, pp. 181-190.
Seebald et al., "Reactions on Alumli.na Oxides, 2nd Notice.: Reactions of butan-2-one on aluminum oxide ", Arch. Pharmaz., vol. 305, No. 10, 1972, 18 pages (9 pages of English Translation and 9 pages of Official Copy).
Shimizu et al., "Direct C—C Cross-Coupling of Secondary and Primary Alcohols Catalyzed by a γ-Aiumina-Supported Silver Subnanocluster", Angewandte Chemie International ed. In English, vol. 48, 2009, pp. 3982-3986.
Shimizu et al., "Direct C—C Cross-Coupling of Secondary and Primary Alcohols Catalyzed by a γ-Alumina-Supported Silver Subnanocluster", Angewandte Chemie, vol. 121, 2009, pp. 4042-4046.
Shuikin et al., "Activity of Copper- and Iron-Containing Catalysts in the Reaction of Isophorone with Ammonia and Hydrogen", Petroleum Chemistry, vol. 36, No. 1, 1996, pp. 174-179.
Snell, Rayan William, "Carbon-Carbon Bond Forming Reactions for Bio-Oil Upgrading: Heterogeneous Catalyst and Model Compound Studies", Digital Repository Iowa State University, 2012, 179 Pages.
Tan et al., "Advances in Catalysts of Aldol Condensation", Chemical Industry and Engineering, vol. 23, No. 1, Jan. 2006, pp. 70-74 (English Abstract Submitted).
Yamada et al., "A Solid-Phase Self-Organized Catalyst of Nanopalladium with Main-Chain Viologen Polymers: α-Alkylation of Ketones with Primary Alcohols", Organic Letters, vol. 8, No. 7, 2006, pp. 1375-1378.
Yamada et al., "Development of a Convoluted Polymeric Nanopalladium Catalyst: α-Alkylation of Ketones and Ring-Opening Alkylation of Cyclic 1,3-Diketones with Primary Alcohols", Tetrahedron, vol. 63, 2007, pp. 8492-8498.
International Search Report and Written Opinion received for PCT Patent Application No. PCT/US2015/057901, dated Feb. 4, 2016, 10 pages.

\* cited by examiner

METHODS FOR PRODUCING FUELS, GASOLINE ADDITIVES, AND LUBRICANTS USING AMINE CATALYSTS

CROSS-REFERENCE TO RELATED APPLICATIONS

This application is a U.S. national stage application of PCT/US2015/057901, filed internationally on Oct. 28, 2015, which claims priority to U.S. Provisional Patent Application No. 62/072,383, filed Oct. 29, 2014, which are incorporated herein by reference in their entireties.

FIELD

The present disclosure generally relates to the production of ketones, and more specifically to the production of ketones by reacting methyl ketones with alcohols in the presence of an amine catalyst and a metal catalyst, and such ketone products may be suitable for use as precursors for fuels, gasoline additives, and/or lubricants, and precursors thereof.

BACKGROUND

Transformation of biomass to liquid fuel is desirable to meet the growing demand for transportation fuels in the current diminishing fossil fuel circumstances. As the world's accessible fossil reservoirs are gradually depleted, it is crucial to develop sustainable, long-term strategies based on the utilization of renewable feed stocks. Biomass-derived molecules are inherently oxygen-rich; consequently, the excess oxygen must be removed in order to raise the energy density of the products and make them suitable for transportation fuels.

Some of the main challenges in current transformations of biomass to liquid fuel include sensitivity of such transformations to the concentration of water, and decreases in product yield as the concentration of water present increases. This requires the application of costly additional steps to achieve the desired yield, including the removal of water from reactant fermentation mixtures through distillation and controlling the water content during the reaction. The catalysts used also often have a limited lifetime, requiring high initial catalyst loading or the addition of more catalyst during the reaction.

Thus, what is needed in the art is an alternative process for producing fuels (e.g., gasoline or diesel), gasoline additives, and/or lubricants from biomass.

BRIEF SUMMARY

The present disclosure addresses this need in the art by providing methods for producing ketone products from methyl ketones and alcohols using the amine catalysts described herein. Such ketone products may be used as precursors for fuels, gasoline additives, and/or lubricants. For example, the longer-chain ketones may be converted into alkanes, alcohols, ethers or amines according to methods and techniques known in the art, for use as fuels, gasoline additives, and/or lubricants.

In one aspect, provided is a method of producing ketone products (e.g., longer-chain ketones), by contacting a methyl ketone and at least one alcohol with an amine catalyst and a metal catalyst and producing ketone products (e.g., longer-chained ketones) from at least a portion of the methyl ketone and the at least one alcohol by a condensation reaction. In some embodiments, the methyl ketone is a compound of Formula (A):

wherein:
    $R^1$ is H, alkyl, carbocyclyl, or heterocyclyl,
        wherein the alkyl, carbocyclyl, or heterocyclyl is unsubstituted or substituted with one or more substituents independently selected from hydroxyl, nitro, and halo; and
    x is an integer greater than or equal to 1.

In some variations, the amine catalyst includes an amine moiety having the structure:

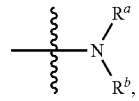

wherein $R^a$ and $R^b$ at each occurrence are independently H, alkyl, carbocyclyl, or heterocyclyl, or ether, or any combinations thereof;
    wherein the alkyl, carbocyclyl, heterocyclyl, or ether is independently unsubstituted or substituted with one or more substituents selected from alkyl, hydroxyl, amine, oxo, carboxyl, imine, carbocyclyl, heterocyclyl, halo, ether, and thioether;
or $R^a$ and $R^b$ are taken together with the nitrogen atom to which they are both attached to form a heterocycle,
    wherein the heterocycle is unsubstituted or substituted with one or more substituents selected from alkyl, hydroxyl, amine, oxo, carboxyl, imine, carbocyclyl, heterocyclyl, halo, ether, and thioether.

In other variations, the amine moiety of the amine catalyst includes a heterocycle containing at least one nitrogen atom, wherein the heterocycle is unsubstituted or substituted with one or more substituents selected from alkyl, carbocyclyl, heterocyclyl, carboxyl, hydroxyl, halo, ether, and thioether.

In certain variations, the amine catalyst further includes a solid support and a linker, wherein the linker attaches the amine moiety to the solid support.

In other aspects, provided herein is also a method of producing ketones (e.g., longer-chain ketones) from a methyl ketone and at least one alcohol, by contacting a methyl ketone and at least one alcohol with any of the amine catalysts described herein, and any of the metal catalysts described herein, wherein the methyl ketone and the at least one alcohol are contacted with the amine catalyst and the metal catalyst in the presence of an acid. The acid may supported (e.g., on a solid support) or unsupported.

In other aspects, provided herein is also a ketone (e.g., a longer-chain ketone) or a mixture of such ketones produced according to any of the methods described herein.

In yet other aspects, provided is a composition that includes a methyl ketone, at least one alcohol, any of the amine catalysts described herein, and any of the metal catalysts herein. In certain embodiments, the composition further includes water. In some embodiments, the composition further includes any of the ketone products (e.g., longer-chain ketones) described herein.

In another aspect, provided herein is a method of contacting a composition that includes biomass and/or sugars with a fermentation host to produce a fermentation product mixture, wherein the fermentation product mixture includes a methyl ketone and at least one alcohol, and contacting the methyl ketone and the at least one alcohol with an amine catalyst and a metal catalyst to produce a mixture of ketones (e.g., longer-chain ketones) from at least a portion of the methyl ketone and the at least one alcohol present in the fermentation product mixture.

In yet another aspect, provided herein is a method of contacting a composition that includes biomass and/or sugars with a fermentation host to produce a fermentation product mixture, wherein the fermentation product mixtures includes acetone, butanol, and ethanol, and contacting the acetone, butanol, and ethanol with an amine catalyst and a metal catalyst to produce a mixture of longer-chain ketones from at least a portion of the acetone, butanol, and ethanol.

In yet another aspect, provided is a method of producing at least one alkane, by:

contacting a methyl ketone and at least one alcohol with an amine catalyst and a metal catalyst to produce a ketone (e.g., a longer-chain ketone), or a mixture thereof; and hydrodeoxygenating the ketone, or a mixture thereof, to produce at least one alkane.

In yet another aspect, provided is a method of producing at least one alcohol, by:

contacting a methyl ketone and at least one alcohol with an amine catalyst and a metal catalyst to produce a ketone (e.g., a longer-chain ketone), or a mixture thereof; and reducing (e.g., hydrogenating) the ketone, or a mixture thereof, to produce at least one alcohol.

Provided is also a composition that includes:

a fuel (e.g., a diesel fuel), a gasoline additive, or a lubricant, or any mixtures thereof; and at least one alkane or at least one alcohol produced according to any of the methods described above, or any mixtures thereof.

Provided is also a fuel or lubricant, comprising: at least one alkane or at least one alcohol produced according to any of the methods described above, or any mixtures thereof.

DESCRIPTION OF THE FIGURES

The present application can be understood by reference to the following description taken in conjunction with the accompanying figures.

DETAILED DESCRIPTION

Figure 1:
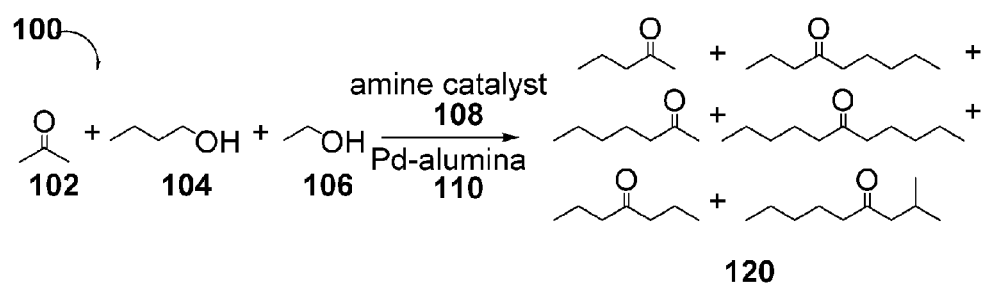
FIG. 1 depicts an exemplary reaction scheme for the condensation of an alcohol-butanol-ethanol (ABE) mixture in the presence of an amine catalyst and a metal catalyst.

The following description sets forth numerous exemplary configurations, processes, parameters, and the like. It should be recognized, however, that such description is not intended as a limitation on the scope of the present disclosure, but is instead provided as a description of exemplary embodiments.

Provided herein are methods of producing ketones from the condensation of a methyl ketone and at least one alcohol using a catalytic system that includes: (i) a metal moiety, (ii) an acidic moiety, and (iii) a basic moiety, which in combination catalyzes the condensation of the methyl ketone with the at least one alcohol. The basic moieties help to activate nucleophiles, and the acidic moieties help activate electrophiles to cooperatively catalyze the condensation of the methyl ketone and the at least one alcohol. In the methods described herein, the basic component includes an amine moiety. The acidic component may be provided as part of the amine catalyst, or separately for use with the amine catalyst. In some variations, the metal catalyst, the basic component, and the acidic component may be the same catalyst, or they may be separately provided. In one variation, the metal catalyst is provided separately from the acidic and basic components provided together.

In some variations, the amine catalyst is supported, and an additional acid may be optionally provided as part of the solid support of the catalyst. In other variations, the acid is provided separately from the solid supported amine catalyst.

For example, in some variations, the amine catalyst includes at least one amine moiety attached to a solid support. In one variation, the solid support has acidic properties. In another variation, the solid support has non-acidic properties, and the method further includes the use of at least one additional acid to produce longer-chain ketones. In yet another variation, the solid support has acidic properties, and the method further includes the use of at least one additional acid to produce longer-chain ketones.

In any of the foregoing variations where acid is added to the reaction mixture, the acid may itself be supported or unsupported.

The metal catalyst may be a supported metal catalyst. In one variation, the metal catalyst may be provided separately from the amine catalyst. In another variation, metal moieties may be impregnated onto the solid support of the amine catalyst, and thus the metal catalyst and amine catalyst are provided together.

The ketones produced according to the methods described herein may be suitable for use as components in fuels (e.g. gasoline, jet, or diesel fuels), fuel additives, or lubricants. The mixture of methyl ketones and alcohols used in the methods described herein may be a mixture of methyl ketones and alcohols obtained from fermentation of biomass and/or sugars. For example, a composition comprising biomass and/or sugars may be fermented to produce acetone-butanol-ethanol (ABE), which may be used in the methods described herein.

In one aspect, provided is a method of contacting a methyl ketone and at least one alcohol with an amine catalyst in the presence of a metal catalyst, to produce a longer-chain ketone from at least a portion of the methyl ketone and alcohol. Such produced ketones can be further converted for use as fuels, fuel additives, lubricants, and other products.

In one variation, combining a methyl ketone and at least one alcohol in the presence of the amine catalysts and metal catalysts described herein produces a mixture of longer-chain ketones. For example, with reference FIG. 1, process 100 depicts an exemplary process to produce ketones from a mixture of acetone, butanol, and ethanol (ABE). The mixture of acetone 102, butanol 104, and ethanol 106 undergoes self-condensation and cross-condensation in the presence of an amine catalyst 108 and a metal catalyst 110 to produce a mixture of longer-chain ketones 120. In certain embodiments, process 100 may be varied. For example, in one embodiment the amine catalyst is a supported amine catalyst. In another embodiment, the mixture of acetone 102, butanol 104, and ethanol 106 is contacted by an amine catalyst 108 and a metal catalyst 110 in the additional presence of an acid. In one embodiment, the additional acid is a supported acid. In another embodiment the additional acid is an unsupported acid.

With reference to FIG. 1, it should be generally understood that one or more steps may be omitted or added to process 100. For example, the mixture of acetone 102, butanol 104, and ethanol 106 may be contacted by an amine catalyst 108 and a metal catalyst 110 in the further presence of a solvent. In another embodiment, the amine catalyst 108 is isolated from the reaction mixture, and then contacted by an additional mixture of acetone 102, butanol 104, and ethanol 106 is contacted by an amine catalyst 108 and a metal catalyst 110.

While FIG. 1 depicts an exemplary process that uses amine catalyst 108 and metal catalyst 110 provided separately, in some variations the amine catalyst and the metal catalyst are provided together. Further, it should generally be understood that a mixture of methyl ketones may be used in the methods described herein, in combination with at least one alcohol, and the resulting products will be a mixture of ketone products formed by a condensation reaction.

Such methyl ketones and alcohols used in the methods described herein may be obtained from any commercially available sources, as well as any methods known to one of skill in the art. For example, acetone-butanol-ethanol (ABE) fermentation can yield a mixture of acetone (as the methyl ketone) and butanol and ethanol (as the alcohols).

With reference to process 100 (FIG. 1), each of the starting materials, the amine catalysts, the metal catalysts, the acid, the solvent and other reagents, as well as the reaction conditions and products are further described below.

The Amine Catalyst

The amine catalyst used in the methods described here include at least one amine moiety. In some variations, the amine catalyst may be a supported catalyst, and further include a solid support. Any suitable amine-containing catalyst that can catalyze the reaction of methyl ketones and alcohols to produce longer-chain ketones may be used herein. Any combinations of the amine catalysts described herein may be used.

Amine Moiety

In some embodiments, the amine catalyst may include a primary amine (e.g., R'—NH$_2$), a secondary amine (e.g., R"R'—NH), or a tertiary amine (e.g., R'''R"R'—N), or any combinations thereof.

In some variations, the amine catalyst includes:

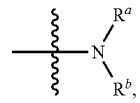

wherein:

R$^a$ and R$^b$ at each occurrence are independently H, alkyl, carbocyclyl, heterocyclyl, or ether, or any combinations thereof;

or R$^a$ and R$^b$ are taken together with the nitrogen atom to which they are both attached to form a heterocycle.

In certain variations, the alkyl, carbocyclyl, heterocyclyl, or ether of R$^a$ and R$^b$ at each occurrence are independently unsubstituted or substituted with one or more substituents selected from alkyl, hydroxyl, amine, oxo, carboxyl, imine, carbocyclyl, heterocyclyl, halo, ether, and thioether. It should be understood that, as used herein, the amine substituent of the amine moiety of the catalyst refers to —NRR', and in some variations, each R and R' is independently H, alkyl, carbocyclyl, or heterocyclyl.

In certain variations, the heterocycle formed when R$^a$ and R$^b$ are taken together is unsubstituted or substituted with one or more substituents selected from alkyl, hydroxyl, amine, oxo, carboxyl, imine, carbocyclyl, heterocyclyl, halo, ether, and thioether.

In some embodiments, either R$^a$ or R$^b$ is H, and the other R$^a$ or R$^b$ is alkyl, carbocyclyl, heterocyclyl, ether, or any combinations thereof. In other embodiments, either R$^a$ or R$^b$ is H, and the other R$^a$ or R$^b$ is alkyl.

In some embodiments, R$^a$ and R$^b$ are independently H, or alkyl. In certain embodiments, R$^a$ is H and R$^b$ is alkyl. In yet other embodiments, R$^a$ and R$^b$ are independently alkyl. In some embodiments, R$^a$ and R$^b$ are independently H, methyl, ethyl, propyl, butyl, pentyl, or hexyl. The alkyl may be branched or unbranched. For example, in one embodiment, R$^a$ and R$^b$ may be independently H, isopropyl, isobutyl, or tert-butyl.

In some embodiments, R$^a$ and R$^b$ are independently H or alkyl substituted with an amine. In one variation, R$^a$ is H and R$^b$ is

In another variation, R$^a$ is H and R$^b$ is

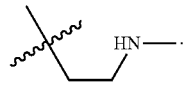 [SMILES: *CCNC]

In other embodiments, R$^a$ and R$^b$ may be taken together with the nitrogen atom to which they are both attached to form a heterocyclyl, wherein the heterocyclyl is unsubstituted or substituted with one or more substituents selected from alkyl, hydroxyl, amine, oxo, carboxyl, imine, carbocyclyl, heterocyclyl, halo, ether, and thioether.

In some embodiments, the amine catalyst includes an unsubstituted or substituted heterocyclyl. For example, in one embodiment, the amine catalyst includes a pyrrolidinyl moiety or a piperidinyl moiety.

In some embodiments, the amine catalyst includes a heterocyclyl that includes at least one nitrogen atom, wherein the heterocyclyl is unsubstituted or substituted with one or more substituents independently selected from alkyl, carbocyclyl, heterocyclyl, carboxyl, hydroxyl, halo, ether, and thioether. For example, in one embodiment, the amine catalyst includes a proline moiety.

In some embodiments, the amine catalyst includes a heterocyclyl containing at least two nitrogen atoms. For example, in one embodiment, the amine catalyst includes a piperazinyl moiety, an imidazolyl moiety, a triazabicyclodecene moiety, or an aminopyridinyl moiety. In other embodiments, the amine catalyst is piperazine, imidazole, triazabicyclodecene, or aminopyridine.

In other embodiments, the amine catalyst includes an —NH$_2$, methylamine, ethylamine, propylamine, dimethylamine, diethylamine, dipropylamine, ethane 1,2-diamine, or N$^1$-(2-aminoethyl)ethane-1,2-diamine moiety, or any combinations thereof. In other embodiments, the amine catalyst includes an imidazole, pyridine, triazabicyclodecene, pyrrolidine, proline, or 4-dimethylaminopyridine moiety, or any combinations thereof. In certain embodiments, the amine catalyst includes a moiety selected from:

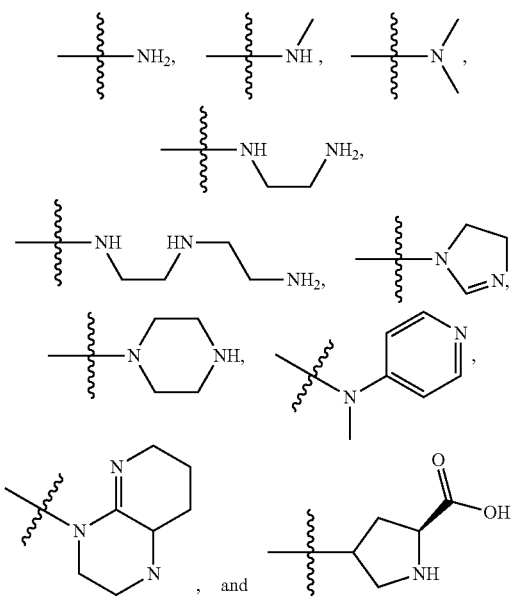

In yet other embodiments, the amine catalyst includes:

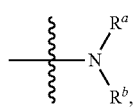

wherein R$^a$ and R$^b$ are independently H or a moiety of Formula (B):

—[(CR$^2$R$^3$)$_f$(NR$^4$)]$_g$—(CR$^5$R$^6$)$_h$NR$^7$R$^8$   (B), wherein:
each R$^2$, R$^3$, R$^4$, R$^5$, R$^6$, R$^7$, and R$^8$ are independently H or alkyl; and
f, g, and h are independently integers greater than or equal to 1.

In one embodiment of the amine catalyst,
R$^a$ is H;
R$^b$ is a moiety of Formula (B), wherein R$^2$, R$^3$, R$^4$, R$^5$, R$^6$, R$^7$, and R$^8$ of the moiety of Formula (B) are each H; and
f is 2, g is 1, and h is 2.

In one variation of the amine catalyst, R$^a$ is H, and R$^b$ is a moiety of Formula (B), wherein the moiety of Formula (B) is

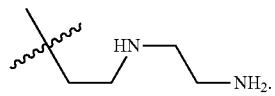

Thus, the amine moiety is

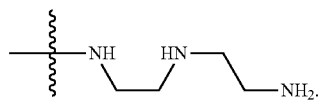

Supported Amine Catalysts

In some embodiments, the amine catalyst is a supported amine catalyst. In certain embodiments, the supported amine catalyst includes an amine moiety attached to a solid support.

In other embodiments, the supported amine catalyst includes a solid support, a linker, and an amine moiety, where the linker attaches the amine moiety to the solid support.

Any suitable methods known in the art to attach the amine moiety to the solid support may be employed. For example, the amine moiety may be attached to the solid support by silylation. An exemplary method to attach an amine moiety to a solid support by silylation is as follows. Silica or silica-alumina supports may be mixed with an organosilane containing an amine moiety, and a solvent. The mixture may then be heated (e.g. at or above 320 K) to modify the support, and the silylated support may be isolated by any method known in the art (e.g. by filtration), optionally washed with solvent, and optionally dried to obtain a support that includes an amine moiety. One of skill in the art would know how to select an appropriate organosilane.

In some embodiments, the solid support is an acidic support. For example, in one variation, the acidic support is silica, alumina, or silica-alumina.

In some variations, the solid support is porous. Examples of suitable porous supports include silica, alumina, silica-alumina, titanium oxides (for example TiO$_2$), zirconium oxides (for example ZrO$_2$), and niobium oxides (for example Nb$_2$O$_5$). In certain variations, the solid support may be a combination of porous and nonporous materials, or may be a material with porous and nonporous regions. In certain variations, the solid support includes silica, alumina, silica-alumina, or any combinations thereof.

In certain embodiments, the solid support is porous having pores with an average diameter between 2 and 50 nm, between 2 and 40 nm, between 2 and 30 nm, or between 2 and 25 nm. In some embodiments, the solid support is porous, wherein the pores have a diameter between 2 and 50 nm, between 2 and 40 nm, between 2 and 30 nm, or between 2 and 25 nm. In other embodiments, the solid support is porous, wherein at least a portion of the pores have a diameter between 2 and 50 nm, between 2 and 40 nm, between 2 and 30 nm, or between 2 and 25 nm.

In some embodiments, the solid support is mesoporous. In some variations, the entire solid support may be mesoporous, or sections of the solid support may be mesoporous. Mesoporous solids include mesoporous silica, mesoporous alumina, mesoporous silica-alumina, or any combinations thereof. Examples of suitable mesoporous solids include MCM-41, SBA-15, and KIT-6. In some variations, mesoporous solids can also include mesoporous oxides of titanium, zirconium, cerium, tin, niobium, and tantalum, or any combinations thereof. In some embodiments, the solid support may be a combination of nonporous and mesoporous materials, or may be a material with mesoporous and nonporous regions.

In some embodiments, the solid support is an acidic support. It should be understood that an "acidic support" is a support that has acidic properties. In some variations, the acidic support includes at least one Brønsted acid site, at least one Lewis acid site, or a combination thereof. For example, silica-alumina has both Brønsted acid sites and Lewis acid sites. Support acidity may be measured by a variety of techniques known to one of skill in the art. For example, acidity of the support may be measured by monitoring pyridine adsorption onto the support through infrared (IR) spectroscopy.

Modification of the Solid Support

The solid support may be modified to include groups other than the amine moiety. The entire solid support or at least a portion of the solid support may be modified to include groups other than the amine moiety.

For example, the solid support may be modified to include silicon, aluminum, germanium, boron, or phosphorous atoms, or any combinations thereof. In some embodiments, the solid support is silica-alumina modified to include silicon, aluminum, germanium, boron, or phosphorous atoms, or any combinations thereof. In one embodiment, the solid support is silica-alumina modified to include additional silicon atoms. In another embodiment, the solid support is alumina modified to include silicon atoms. In yet another embodiment, the solid support is mesoporous silica modified to include additional silicon atoms.

The solid support may be modified to include acid moieties. For example, the solid support may be modified to include a sulfonic acid moiety, a phosphoric acid moiety, a carboxylic acid moiety, or any combinations thereof. In some embodiments, the solid support is silica-alumina modified to include a phosphoric acid moiety, a carboxylic acid moiety, or a sulfonic acid moiety. Any suitable methods known in the art to modify the solid support of the amine catalyst to include acid moieties may be employed. For example, silica and silica-alumina supports may be modified with organosilane compounds containing acid moieties. An exemplary method to modify a solid support with an organosilane compound containing an acid moiety is as follows. Silica or silica-alumina supports may be mixed with an organosilane containing an acid moiety, and a solvent. The mixture may then be heated (e.g. at or above 320 K) to modify the support, and the modified support may be isolated by any method known in the art (e.g. by filtration), optionally washed with solvent, and optionally dried to obtain a support that has been modified to include an acid moiety. One of skill in the art would recognize how to select the appropriate organosilane.

The solid support may also be modified by silylation. For example, in some variations, the solid support is silica-alumina that has undergone silylation. Any suitable methods known in the art to modify the solid support of the amine catalyst to include silyl moieties may be employed. For example, silica and silica-alumina supports may undergo silylation with organosilane compounds. An exemplary method to prepare a silylated solid support is as follows. Silica or silica-alumina supports may be mixed with an organosilane, and a solvent. The mixture may then be heated (e.g. at or above 320 K) to modify the support, and the modified support may be isolated by any method known in the art (e.g. by filtration), optionally washed with solvent, and optionally dried to obtain a support that has been silylated. One of skill in the art would know how to select an appropriate organosilane (e.g. methyltrimethoxysilane).

The solid support may be modified to include more than one group other than the amine moiety. For example, in some embodiments, the solid support is modified to include a sulfonic acid moiety, and has undergone silylation. In other embodiments, the solid support is modified to include additional silicon atoms, and to include a carboxylic acid moiety. In yet other variations, the solid support is modified to include a phosphoric acid moiety, silicon atoms, and has undergone silylation. In certain variations, the solid support is modified to include a phosphoric acid moiety, a carboxylic acid moiety, silicon atoms, and phosphorous atoms. In one embodiment, the solid support is silica-alumina modified to include additional silicon atoms, and that has undergone silylation. In another embodiment, the solid support is alumina modified to include silicon atoms, and that has undergone silylation.

Any suitable methods known in the art to modify the solid support of the amine catalyst to include more than one group other than the amine moiety may be employed. For example, the solid support may be modified by more than one organosilane compound. An exemplary method to prepare a solid support modified by more than one group other than the amine moiety is as follows. Silica or silica-alumina supports may be mixed with an organosilane containing an acid moiety, and a solvent. The mixture may then be heated (e.g. at or above 320 K) to modify the support, and the modified support may be isolated by any method known in the art (e.g. by filtration), optionally washed with solvent, and optionally dried to obtain a solid support that has been modified to include an acid moiety and additional silicon atoms. One of skill in the art would know how to select an appropriate organosilane.

Linker

The amine catalysts described herein may, in some embodiments, have a linker connecting the solid support and the amine moiety. In one variation, the linker, when present, may include -alkyl-, -aliphatic-, -aryl-, -carbocycle-, -heterocyle-, -sulfone-, or -ether-, or any combinations thereof.

It should be understood that, as used herein, -moiety- refers to a moiety having bivalency. For example, -alkyl- refers to an alkyl moiety with bivalency. For example, "-propyl-" refers to $-CH_2CH_2CH_2-$, "-butyl-" refers to $-CH_2CH_2CH_2CH_2-$, and "-pentyl-" refers to $-CH_2CH_2CH_2CH_2CH_2-$.

Similarly, -ether- refers to an ether moiety with bivalency. For example, "-ethoxyethane-" refers to $-CH_2CH_2OCH_2CH_2-$.

In one embodiment, the linker is -propyl-, -butyl-, -pentyl-, -hexyl-, -heptyl-, -octyl-, -nonyl-, or -decyl-. In one embodiment, the linker is -propyl-.

In some embodiments, the linker may be unsubstituted, or substituted with one or more groups independently selected from alkyl, hydroxyl, amine, oxo, carboxyl, imine, carbocyclyl, and heterocyclyl.

In one variation, the linker may be -ether-substituted with a hydroxyl group. In one variation, the linker is

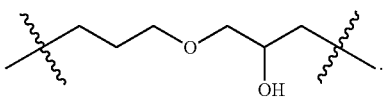 [SMILES: *CCCOCC(O)C*]

In one embodiment, the linker includes a combination of -alkyl-, -carbocycle-, and -sulfone-. For example, in one embodiment the linker is

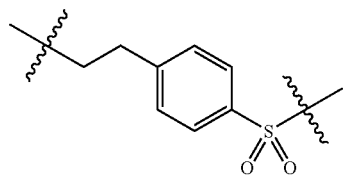

The linker has a certain length between the amine moiety and the solid support. The length of the linker may affect the activity of the supported amine catalyst, and affect product yield. In some embodiments, the linker includes 3, 4, 5, 6, 7, 8, 9, or 10 linear chain atoms. In one embodiment, the linker includes at least 3 linear chain atoms. Linkers with 3 linear chain atoms include

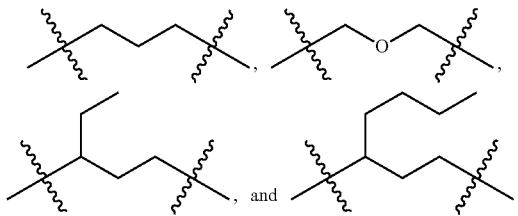

In some variations, the linker is attached to the solid support of the amine catalyst. In some embodiments, the linker is attached to the solid support through a C—Si, C—B, C—Ge, or C—P bond. For example, a -propyl- linker may, at one end of the linker, be attached through a C—Si bond to a Si atom on the solid support, while the other end of the linker is attached to the amine moiety. For example, the support may be modified by silylation to include additional Si atoms.

Any suitable methods known in the art to attach the linker to the solid support may be employed. For example, the linker may be attached to the solid support by silylation, wherein the organosilane includes the linker. An exemplary method to attach a linker to a solid support is as follows. Silica or silica-alumina supports may be mixed with an organosilane, and a solvent. The mixture may then be heated (e.g. at or above 320 K) to modify the support, and the modified support may be isolated by any method known in the art (e.g. by filtration), optionally washed with solvent, and optionally dried to obtain a solid support modified to contain a linker, wherein the linker is attached to the solid support through a C—Si bond.

In certain embodiments, the solid support has been modified to contain a Si, B, Ge, or P atom, and the linker is bound to that Si, B, Ge, or P atom. For example, silica-alumina may be modified to contain additional Si atoms, and the linker may be bound to one of those additional Si atoms. Any suitable methods known in the art to modify the solid support of the amine catalyst to include Si, B, Ge, or P atoms may be employed. For example, the support may be modified by silylation to include additional Si atoms. An exemplary method to modify a solid support to include additional Si atoms is as follows. Silica or silica-alumina supports may be mixed with an organosilane, and a solvent. The mixture may then be heated (e.g. at or above 320 K) to modify the support, and the modified support may be isolated by any method known in the art (e.g. by filtration), optionally washed with solvent, and optionally dried to obtain a solid support modified by silylation to include additional Si atoms.

The supported amine catalyst may be used in combination with one or more additional acids. Suitable acids are described in further detail below.

Properties of an Amine Catalyst

The amine catalysts described herein help to catalyze the condensation of methyl ketones and alcohols in the presence of water. Water may be present in the reaction mixture for various reasons. For example, water can be produced as a byproduct of the condensation reaction. Water may be present in the starting materials used. For example, in some embodiments, the methyl ketone(s) and/or alcohol(s) are provided in a fermentation mixture, which can also include water.

Enamine Complex

In some variations, the condensation of methyl ketones and alcohols catalyzed by the amine catalysts described herein may proceed through an enamine complex, or any tautomers thereof. An enamine includes both an alkene and an amine functional group, and may be represented as follows:

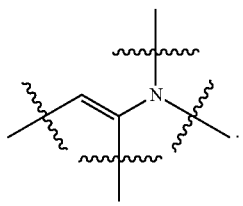 [SMILES: */C=C(\*)N(*)*]

In some variations, the enamine may tautomerize to form an imine. An imine includes a C=N bond.

Thus, in some embodiments, described herein are methods of producing ketone(s) (e.g., longer-chain ketone(s)), by contacting a methyl ketone and at least one alcohol with an amine catalyst and a metal catalyst to form an enamine complex, and producing ketone(s) from the enamine complex. It should generally be understood that a mixture of methyl ketones may also be used in the methods described herein.

In some embodiments, the amount of water present in the reaction mixture is at least 99 wt %, at least 90 wt %, at least 80 wt %, at least 70 wt %, at least 60 wt %, at least 50 wt %, at least 40 wt %, at least 30 wt %, at least 20 wt %, at least 10 wt %, at least 5 wt %, at least 1 wt %, at least 0.1 wt %, or at least 0.01 wt %. In other embodiments, the amount of water present in the reaction mixture is at least 99 wt %, at least 90 wt %, at least 80 wt %, or at least 70 wt %. In certain embodiments, the amount of water present in the reaction mixture is between 1 wt % and 60 wt %. In some embodiments, the amine catalysts and metal catalysts described herein may catalyze the condensation of methyl ketones and alcohols in the absence of water.

While the condensation reaction may be carried out in the presence of water, in other embodiments, water produced during the reaction may also be controlled or removed. Water produced during the reaction may be controlled or removed using any suitable methods or techniques known in the art. For example, water produced during the reaction may be controlled or removed by distillation (e.g., using a Dean-Stark apparatus) or by the use of a biphasic reaction system.

Additional water may also be present in the reaction mixture from the starting materials provided. For example, the methyl ketone(s) and/or alcohol(s) may be obtained from a fermentation product mixture, and the fermentation product mixture may additionally contain water. For example, in the condensation of acetone, butanol, and ethanol (ABE), the ABE reactant mixture may be obtained from a fermentation broth, and the fermentation broth may additionally contain water. Thus, provided herein is also a method of contacting biomass with a fermentation host to produce a fermentation product mixture, wherein the fermentation product mixture includes methyl ketone(s) and alcohol(s), and contacting the fermentation product mixture with an amine catalyst and a metal catalyst as described herein to produce ketone products (e.g., longer-chain ketone(s)) from the condensation of the methyl ketone(s) and the alcohol(s). In some embodiments, the fermentation host is selected from fungi and bacteria.

Catalyst Lifetime

The lifetime of the catalyst used may be described in various ways. In some variations, the lifetime of the amine catalysts may be described based on the yield of ketones produced over a period of time. In certain variations, the lifetime may also be expressed based at a given catalyst loading. In yet other variations, the lifetime of the amine catalyst may be described based on the yield based on the amount of water present in the reaction mixture.

As used herein, the term "yield" refers to the total amount of product expressed in a percentage (%) relative to the amount of methyl ketone or alcohol reactant present in the starting reaction mixture. For example, where multiple ketone compounds are produced, the overall reaction yield refers to the combined molar yields of the ketone products, calculated with respect to the molar amount of methyl ketone or alcohol reactant present in the starting reaction mixture.

In certain embodiments, the amine catalyst and metal catalyst system has less than a 50%, less than a 40%, less than a 30%, less than a 20%, or less than a 10% reduction in yield over a 16 h period. In one embodiment, the amine catalyst and metal catalyst system has less than a 20% reduction in yield over 16 h.

In certain embodiments, the amine catalyst and metal catalyst system has less than a 50%, less than a 40%, less than a 30%, less than a 20%, or less than a 10% reduction in yield when water is present at a concentration between 1 mol % and 60 mol %. In one embodiment, the amine catalyst and metal catalyst system has less than a 20% reduction in yield when water is present at a concentration between 1 mol % and 20 mol %.

In yet other embodiments, the product yield produced from reactants in the presence of the amine catalyst and metal catalyst may vary both over time and with the amount of water present. In some embodiments, the amine catalyst and metal catalyst system has less than a 50%, less than a 40%, less than a 30%, less than a 20%, or less than a 10% reduction in yield when water is present at a concentration between 1 mol % and 60 mol %. In one embodiment, the amine catalyst and metal catalyst system has less than a 20% reduction in yield over a 16 h period when water is present at a concentration between 1 mol % and 20 mol %.

In some embodiments, the methyl ketone and/or alcohol is obtained from a fermentation product mixture, and the fermentation product mixture may additionally contain water. Thus, provided herein is also a method of contacting biomass with a fermentation host to produce a fermentation product mixture, wherein the fermentation product mixture includes a methyl ketone and an alcohol, and contacting the fermentation product mixture with an amine catalyst and metal catalyst as described herein to produce a longer-chain ketone from the condensation of the methyl ketone and the alcohol. In some embodiments, the fermentation host is selected from fungi and bacteria.

In certain embodiments, the product yield produced from reactants in the presence of the amine catalyst varies with the ratio of reactant to catalyst. The ratio may be described with different expressions for different systems, for example weight hour space velocity (WHSV) and liquid hour space velocity (LHSV). As used herein, WHSV refers to the weight of reactant feed per unit weight of the catalyst per hour. As used herein, LHSV refers to the weight of liquid reactant feed per unit weight of the catalyst per hour. One of skill in the art would recognize how to convert the WHSV values into the LHSV, and vice versa.

The Acid

In some embodiments, at least one acid is combined with the amine catalysts described herein to convert the methyl ketone(s) and alcohol(s) into ketone product(s). The acid may be a supported or unsupported acid.

In one embodiment, the amine catalyst includes a solid support having acidic properties, and at least one acid is optionally used in the methods described herein. In another embodiment, the amine catalyst includes a solid support having non-acidic properties, and the amine catalyst is used in combination with at least one acid.

Suitable acids may include organic acids and inorganic acids. Examples of suitable organic acids may include acetic acid, benzoic acid, terephthalic acid, phthalic acid, isophthalic acid, adipic acid, succinic acid, oxalic acid, pimelic acid, valeric acid, muconic acid, mucic acid, toluic acid, and citric acid, or any combinations thereof. Examples of inorganic acids may include hydrochloric acid, nitric acid, sulfuric acid, boric acid, phosphoric acid, or any combinations thereof. Any combination of the acids described herein may be used.

In one variation, the acid is supported. Supported acids include solid supports which contain acidic groups. Examples of supported acids may include alumina, silica, silica-alumina, titanium oxides (for example $TiO_2$), zirconium oxides (for example $ZrO_2$), and niobium oxides (for example $Nb_2O_5$). It should generally be understood that when both the amine catalyst and the acid are supported, the solid supports of the amine catalyst and the acid may be the same or different. For example, in one variation, both the amine catalyst and the acid include silica-alumina.

In other variations, the supported acid is a solid support that has been modified to include an acid moiety. Examples of acid moieties that may be present on such supports include a sulfonic acid moiety, a phosphoric acid moiety, and a carboxylic acid moiety. For example, a support may be modified such that 4-ethylbenzenesulfonic acid is attached to the support. In one variation, the amine catalyst is supported on silica-alumina, and additional silica-alumina is added without an amine moiety, which has been modified to contain a phosphoric acid moiety.

Suitable unsupported acids include acetic acid, benzoic acid, terephthalic acid, phthalic acid, isophthalic acid, adipic acid, succinic acid, oxalic acid, pimelic acid, valeric acid, muconic acid, mucic acid, toluic acid, citric acid, hydrochloric acid, nitric acid, sulfuric acid, boric acid, and phosphoric acid, or any combinations thereof. Any combinations of the acids described herein may be used. In one variation, the additional acid is acetic acid. In another variation, the additional acid is benzoic acid. In yet another variation, both acetic acid and benzoic acid are added as two additional acids.

The Metal Catalyst

Ketones (e.g., longer-chain ketones) can be produced according to the methods described herein by combining methyl ketone(s) and alcohol(s) with an amine catalyst and a metal catalyst; or a catalyst that includes an amine moiety and a metal moiety (e.g., a catalyst in which the metal is impregnated on the solid support of the amine catalyst).

With reference again to FIG. 1, in some variations, the metal catalyst 110 may be palladium supported on alumina, and in other variations a different metal catalyst may be used. For example, in some variations the metal catalyst is palladium supported on alumina, while in other variations the catalyst is copper supported on silica. In some embodiments, the metal catalyst is palladium supported on silica-alumina. In other embodiments, the metal catalyst is Pd/Ag supported on carbon. In yet other embodiments, the metal catalyst is Pd/Cu supported on $TiO_2$. In some variations, the metal catalyst is a metal impregnated or deposited on a solid support.

In other embodiments, the metal catalyst includes a transition metal. In some embodiments, the metal-based catalyst includes a late transition metal. In some embodiments, the metal catalyst includes a metal selected from ruthenium, iron, palladium, platinum, cobalt, and copper. Mixtures of these metals are also contemplated, including for example metal alloys. In some embodiments, the ruthenium, iron, palladium, platinum, cobalt, and copper, either used alone or in combination, may also be combined with other metals such as lanthanides. In some embodiments, the metal is selected from ruthenium, palladium, and copper. In other embodiments, the metal is palladium or copper. In some embodiments, the metal is copper.

In other embodiments, the metal catalyst may include transition metals such as nickel, ruthenium, rhodium, palladium, rhenium, iridium, or platinum. In other embodiments, the metal catalyst includes palladium or platinum. In certain embodiments, the metal catalyst is $[Ir(COD)Cl]_2$, $RuCl_2(COD)$, $PtCl_2(COD)$, $[Rh(COD)Cl]_2$, Ni/Si-Alumina, Ru/C, Rh/C, Pt/C, or Pd/C.

In some embodiments, the metal catalyst is a single component metal oxides alkaline earth oxides such as alkali metal oxides rare earth oxides (e.g., $ThO_2$, $ZrO_2$, ZnO, and $TiO_2$).

In yet other embodiments, the metal catalyst is a palladium-based catalyst. Palladium-based catalysts may include palladium metal, and complexes of suitable ligands including those containing P and/or N atoms for coordinating to the palladium atoms, and other simple palladium salts either in the presence or absence of ligands. Palladium-based catalysts may also include palladium and palladium complexes supported or tethered on solid supports, such as palladium on carbon (Pd/C), as well as palladium black, palladium clusters, or palladium clusters containing other metals. Suitable examples of palladium-based catalysts may include $Pd(OAc)_2$, $Pd_2(dba)_3$, $Pd(OH)_2/C$, Pd/C, $Pd/CaCO_3$, Pd/Alumina, and Pd-polyethylenimines on silica.

In some embodiments, a combination of one or metals may be used, such as metal alloys. In some embodiments, the combination of one or metals is Pd and Cu. In some embodiments, the metal catalyst contains Pd/Cu, in which Pd is present in molar excess of Cu. In other embodiments, the metal catalyst contains Pd/Cu, in which Cu is present in molar excess of Pd. In yet other embodiments, the metal catalyst contains Pd/Cu at a molar ratio of between 10:1 and 1:10. In one embodiment, the metal catalyst contains Pd/Cu at a molar ratio of 1:1, 2:1, 3:1, 4:1, 5:1, 1:2, 1:3, 1:4, or 1:5. In a certain embodiment, the metal catalyst contains Pd/Cu at a 2:1 molar ratio. In other embodiments, the combination of one or more metals is Pd and Ag.

In some embodiments, the metal catalyst may be a solid-supported metal catalyst. A solid-supported metal catalyst used herein typically is metal catalyst where the metal is deposited or impregnated onto a support.

In some embodiments, the metal catalyst support is selected from hydrotalcite, single component metal oxides, alkaline earth oxides, alkali metal oxides, rare earth oxides, $ThO_2$, MgO, Na doped MgO, SrO, BaO, CaO, ZnO, $La_2O_3$, $TiO_2$, $ZrO_2$, $Al_2O_3$, $SiO_2$—$Al_2O_3$, hydroxyapatite, fluorapatite, tert-butoxyapatite, sepiolite, basic zeolites, alkali ion-exchanged zeolites, alkali ion-added zeolites, Pd/NaY zeolite, $Pd/NH_4$-β zeolite, supported alkali metal ions, alkali metal ions on alumina, alkali metal ions on silica, alkali metal on alkaline earth oxide, alkali metals and alkali metal hydroxides on alumina, $Metal/SiO_2$, $Na/SiO_2$ $Pd/Na/SiO_2$, $Na/Ca/SiO_2$, $Na/Ca/SiO_2$, $Cs/SiO_2$, metal-supported zeolite, potassium oxide supported on zeolite Y, synthetic chrysotiles, $Mg_3(OH)_4Si_4O_5$, cobalt(II)-substituted chrysotile, amino-functionalized mesoporous silica, amino-functionalized MCM-41, alkali ion-exchanged mesoporous silica, alkali ion-exchanged SBA-15, ionic liquid supported MgO, amorphous aluminophosphate, synthetic talcs, magnesium organo silicates, KF supported on alumina, lanthanide imide on zeolite, and lanthanide nitride on zeolite. In some embodiments, the support is an alkali exchanged zeolite such as NaY, KY, RbY, CsY, NaX, KX, RbX, and CsX. In some embodiments a metal such as Pd or Cu is deposited on the alkali exchanged zeolite and used as the metal based catalyst such as, for example, Pd/CsY and Cu/CsY. In some embodiments, alkali metal ions are added to the support (e.g., alkali metal ions on alumina, alkali metal ions on silica, alkali metal on alkaline earth oxide, alkali metals and alkali metal hydroxides on alumina).

In some embodiments, the metal catalyst support is a hydrotalcite. In some embodiments, the hydrotalcite comprises one or more metals selected from magnesium, aluminum, lithium, zinc, copper, and nickel. In other embodiments, the one or more metals are selected from palladium, copper, nickel, zinc, ruthenium, cobalt, and platinum. In some embodiments, the hydrotalcite is selected from Mg—Al, Li—Al, Zn—Al, Cu—Zn—Al, and Ni—Mg—Al hydrotalcite.

Uses of the Amine and Metal Catalysts

Methyl Ketone

A mixture of ketones are produced according to the methods described herein by combining a methyl ketone and an alcohol with an amine catalyst and a metal catalyst. Such ketone products are typically longer in chain length compared to the methyl ketone starting material. While FIG. 1 depicts the use of acetone 102, other methyl ketones may be used.

The methyl ketone may have the structure of Formula (A):

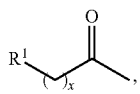
(A)

wherein:
R$^1$ is H, alkyl, carbocyclyl, or heterocyclyl;
x is an integer greater than or equal to 1.

In some variations, the alkyl, carbocyclyl, or heterocyclyl of R$^1$ is unsubstituted or substituted with one or more substituents selected from hydroxyl, nitro, and halo.

In some embodiments of the methyl ketone having the structure of Formula (A), R$^1$ is alkyl. In certain embodiments, R$^1$ is unsubstituted alkyl. For example, R$^1$ may be methyl, ethyl, propyl, butyl, pentyl, hexyl, heptyl, octyl, nonyl, decyl, undecyl, or dodecyl. In certain embodiments, R$^1$ is alkyl substituted with one or more substituents selected from hydroxyl, nitro, chloro, bromo, and iodo.

In certain embodiments of the ketone having the structure of Formula (A), when R$^1$ is alkyl, the alkyl may be unbranched or branched. In some embodiments, the alkyl is branched. In certain embodiments, R$^1$ is isopropyl, isobutyl, tert-butyl, isopentyl, or tert-pentyl.

It should be understood that when R$^1$ is H and x is 1, the methyl ketone having the structure of Formula (A) is acetone. In some embodiments, when R$^1$ is H, x is an integer greater than 1, and the methyl ketone having the structure of Formula (A) is a methyl ketone other than acetone. In other embodiments, when R$^1$ is other than H, x is an integer greater than or equal to 1, and the methyl ketone having the structure of Formula (A) is a methyl ketone other than acetone.

In certain embodiments, x is an integer between 1 and 50, 1 and 40, 1 and 30, 2 and 30, or 3 and 30.

In certain embodiments of the methyl ketone having the structure of Formula (A), R$^1$ is carbocyclyl, or heterocyclyl.

Examples of methyl ketones that may be used in the methods described herein include:

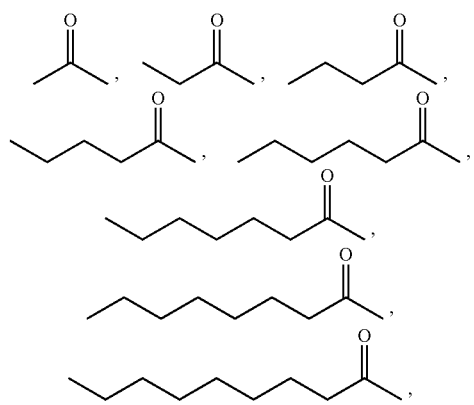

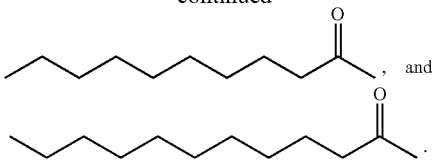

Alcohol

While FIG. 1 depicts the use of butanol 104 and ethanol 106, in other embodiments, other alcohols may be used. For example, in some embodiments, n-propanol is used, while in other embodiments, n-pentanol is used. In some variations, the alcohol is a primary alcohol (e.g., R'—CH$_2$—OH), or a mixture of primary alcohols. Suitable primary alcohols may include, for example, ethanol, n-propanol, n-butanol, or 2-methylpropan-1-ol.

It should be further understood that, in some embodiments, one or more of the alcohols used herein may include one or more —OH groups. In some embodiments, one or more of the alcohols is of Formula (D):

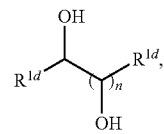
(D)

wherein n is 0 or 1 or 2 and R$^{1d}$ is CH$_3$ or H. In some embodiments, one of the alcohols is glycerol. In certain embodiments, at least one of the —OH groups is bonded to the carbon atom adjacent to a terminal methyl group.

One or more of the alcohols used in the methods described herein may independently be linear or branched. In some embodiments, all linear alcohols may be used. For example, in one embodiment, a mixture of n-butanol and ethanol may be used. In other embodiments, all branched alcohols may be used. In yet other embodiments, a mixture of linear and branched alcohols may be used.

Additionally, one or more of the alcohols used in the methods described herein may be optionally substituted. In some embodiments, one or more of the alcohols may be substituted with 1 to 5 substituents, 1 to 4 substituents, 1 to 3 substituents, 1 to 2 substituents, or 1 substituent. Suitable substituents may include, for example, alkyl, cycloalkyl, aryl, heteroaryl, alkenyl, alkynyl, oxo, —OH, or esters. In some embodiments, any substituent that is not destroyed by base/reduction is contemplated (e.g., aryl or heteroaryl). In other embodiments, any substituent that may be hydrolyzed (e.g., esters) or reduced (e.g., alkenyl or alkynyl) is contemplated. In some embodiments, one or more of the alcohols are unsubstituted. In other embodiments, one or more of the alcohols are substituted. In yet other embodiments, a mixture of unsubstituted and substituted alcohols may be used. For example, in one embodiment, a mixture of acetoin, n-butanol and ethanol may be used.

In some embodiments, the alcohols used herein may contain a primary alcohol moiety (e.g., —R'—CH$_2$—OH).

It should be understood that, while FIG. 1 depicts the use of two alcohols, in some variations a different number of alcohols is used. For example, in some embodiments, one alcohol is used, while in other embodiments, three alcohols are used. Various mixtures of alcohols may be used in the methods described herein. In some embodiments, the alcohols are $C_1$-$C_{20}$ alcohols, $C_2$-$C_{10}$ alcohols, $C_2$-$C_8$ alcohols, $C_2$-$C_6$ alcohols, or $C_2$-$C_4$ alcohols. In one embodiment, the alcohol is butanol. In another embodiment, the alcohol is ethanol. In yet another embodiment, the alcohols include butanol and ethanol.

In some embodiments, one or more primary alcohols are independently $C_1$-$C_{20}$ alcohols, $C_2$-$C_{10}$ alcohols, $C_2$-$C_8$ alcohols, $C_2$-$C_6$ alcohols, or $C_2$-$C_4$ alcohols. In some embodiments, one or more primary alcohols are n-butanol, ethanol, or 2-ethyl-hexanol, or any combination thereof.

In some embodiments, the one or more primary alcohols are butanol and ethanol. In some embodiments, the butanol is provided in stoichiometric excess of the ethanol.

In some embodiments, at least 2%, 5%, 10%, 12%, 15%, 20%, or 25% of the mixture of longer-chain ketones produced from the condensation of a methyl ketone and at least one alcohol is $C_{7+}$ ketones. In certain embodiments, at least 10%, 12%, 15%, or 20%, of the mixture of ketones produced is $C_{7+}$ ketones.

In other embodiments, at least 2%, 5%, 10%, 12%, 15%, 20%, 25%, 30%, or 35% of the mixture of longer-chain ketones produced is $C_{5+}$ ketones. In other embodiments, at least 15%, 20%, 25%, or 30% of the mixture of ketones produced is $C_{5+}$ ketones.

In yet another embodiments, at least 10%, 12%, 15%, or 20% of the mixture of ketones produced is $C_{7+}$ ketones, and at least 15%, 20%, 25%, or 30% of the mixture of ketones produced is $C_{5+}$ ketones.

While FIG. 1 depicts six different ketones in the product mixture 120, in other embodiments the product mixture may contain a different number of longer-chain ketones. For example, in some embodiments, one longer-chain ketone is produced, while in other embodiments, two longer-chain ketones are produced. In certain embodiments, 1, 2, 3, 4, 5, 6, 7, or 8 longer-chain ketones are produced.

Fermentation Product Mixtures

The methyl ketone(s) and alcohol(s) provided for use in the methods described herein may be obtained from any commercially available sources, or accordingly to any methods generally known by one of skill in the art. In some embodiments, the methyl ketone(s) and alcohol(s) are produced from biological processes, such as by fermentation. For example, a fermentation product mixture may include an acetone-butanol-ethanol (ABE) mixture, which may be used as the methyl ketone-alcohol starting material in the reaction to produce longer-chain ketones. With reference to FIG. 1, in some variations the acetone 102, butanol 104, and ethanol 106 are provided in a fermentation product mixture.

In some embodiments, an acetone-butanol-ethanol (ABE) mixture is used as the methyl ketone-alcohol starting materials in the reaction to produce hydrocarbon ketones. In some embodiments, the ABE feedstock may be enriched in butanol and 2-ethylhexanol by reacting ethanol and butanol in a Guerbet reactor prior to feeding the materials to the main alkylation reactor.

The fermentation product mixture described herein may be derived from renewable sources, such as biomass. In some embodiments, the biomass is first converted into sugars, which is then used as the feedstock to produce the fermentation product mixture. In other embodiments, a mixture including sugars derived from biomass may be used as the feedstock to produce the fermentation product mixture. Sugars suitable for use as feedstock to produce the fermentation product mixture may include, for example, monosaccharides, disaccharides, or oligosaccharides. In certain embodiments, the sugars may include any $C_5$ saccharides or $C_6$ saccharides, or a combination of $C_5$ and $C_6$ saccharides. In other embodiments, the sugars may include arabinose, lyxose, ribose, xylose, ribulose, xylulose, allose, altrose, glucose, sucrose, cellobiose, mannose, gulose, idose, galactose, talose, psicose, fructose, sorbose, tagatose, xylobiose, glucose oligomers, xylose oligomers, or a mixture thereof. In one embodiment, the sugars may include glucose, sucrose or xylose, or a mixture thereof. In another embodiment, the sugars may include glucose or sucrose, or a mixture thereof. Any methods known in the art may be employed to produce sugars from the biomass. For example, the biomass may undergo pretreatment processes known in the art to more effectively liberate sugars from the biomass. The biomass is typically made up of organic compounds that are relatively high in oxygen, such as carbohydrates, and may also contain a wide variety of other organic compounds. In some embodiments, the biomass is made up of cellulose, hemicellulose, and/or lignin. Other suitable carbon sources for fermentation may include, for example, pectin, whey, butyric and acetic acids.

It should be understood, however, that in other embodiments, the sugars used as feedstock in the fermentation process may be derived from non-renewable sources, or from both renewable and non-renewable sources.

Acetone-Butanol-Ethanol (ABE) Fermentation Product Mixture

In some embodiments, the fermentation product mixture may include a methyl ketone and one or more alcohols. In certain embodiments, the fermentation product mixture may include a methyl ketone and one alcohol, or a methyl ketone and two alcohols. In certain embodiments, the methyl ketone is acetone. In certain embodiments, the one or more alcohols may be one or more primary alcohols. In one embodiment, the one or more alcohols may be one or more $C_1$-$C_{20}$, $C_1$-$C_{15}$, $C_1$-$C_{10}$ or $C_1$-$C_8$ primary alcohols. The fermentation product mixture may be an ABE mixture produced by fermenting sugars using any host capable of producing hydrocarbons (e.g., ethanol and heavier hydrocarbons). For example in some embodiments, the fermentation host is bacteria from the Clostridia family (e.g., Clostridium acetobutylicum, Clostridium beijerinckii). Clostridia bacteria have the ability to convert biomass-derived carbohydrates into an ABE mixture from both hexoses and pentoses. It should be understood, however, that any fermentation host capable of converting sugars into a mixture of a ketone and one or more alcohols may be employed to provide the starting materials for the process described herein. For example, in some embodiments, the fermentation host is fungi.

In some embodiments, the fermentation product mixture may be used without further purification or isolation steps after the fermentation process. In other embodiments, the fermentation product mixture is isolated after the fermentation process. Any techniques known in the art may be used to isolate the fermentation product mixture (e.g., ABE mixture) after the fermentation process.

While an ABE mixture may be used as starting materials, the starting materials used in the process described herein are not limited to butanol and ethanol as the alcohols. The alcohols may be any length. In some embodiments, the fermentation product mixture may include primary alcohols including, for example, methanol, ethanol, propanol, 2-methylpropan-1-ol, butanol, pentanol, and 2-ethyl-1-hexanol.

In some embodiments, the ABE mixture has a mass ratio of about 3 to about 6 to about 1, but the ratio of acetone to the two or more primary alcohols may vary. For example, the fermentation process may be optimized to reduce the amount of ethanol produced, so as to maximize butanol yields.

Additional methyl ketones and alcohols may be added to the fermentation product mixture to vary the range of molecular weights and structures obtained from the process described herein. In some embodiments, these additional methyl ketones and alcohols may be added to the fermentation product mixture before use in the reaction with the catalyst. In other embodiments, these additional methyl ketones and alcohols may be added during the reaction. These additions to the fermentation product mixture may be useful for improving the product properties for specific applications, such as biodiesel. The alcohols and methyl ketones added to the fermentation product mixture may be saturated or unsaturated.

The fermentation product mixture may also include bio-derived ketones through ketonization of volatile fatty acids. For example, acetic acid may be ketonized via fermentation to form acetone, which can be converted into a mix of higher ketones using the methods described herein to produce gasoline and gasoline precursors. Propionic acid may also be ketonized via fermentation to form 3-pentanone, which can be converted into a mix of higher ketones using the methods described herein to produce gasoline and gasoline precursors.

One or more of the methyl ketones and alcohols described herein may be provided by a fermentation product mixture. In some embodiments, the methyl ketone of Formula (A) is provided by a fermentation product mixture, and the alcohol is added to the fermentation product mixture. In other embodiments, the alcohol is provided by a fermentation product mixture, and the methyl ketone of Formula (A) is added to the fermentation product mixture. In yet other embodiments, both the methyl ketone and the alcohol are provided by a fermentation product mixture. In other embodiments, the methyl ketone is provided by one fermentation product mixture, and the alcohol is provided by a separate fermentation product mixture.

It should be understood that, in some embodiments, one methyl ketone having a structure of Formula (A), as described above may be used. Such ketone can undergo condensation with an alcohol to produce the longer-chain ketones described herein. In other embodiments, however, a mixture of methyl ketones independently having the structure of Formula (A) may be used. Such mixture of ketones can undergo different condensation reactions with the alcohol to produce a mixture of different products.

It should be understood that, in some embodiments, one alcohol may be used as described above may be used. Such alcohol can undergo condensation with a methyl ketone to produce the longer-chain ketones described herein. In other embodiments, however, a mixture of alcohols may be used. Such mixture of alcohols can undergo different condensation reactions with the methyl ketone to produce a mixture of different products.

It should be further understood that in some embodiments, a mixture of methyl ketones and alcohols is used. Thus, provided herein is also a method for producing longer-chain ketones by contacting one or more methyl ketones independently having a structure of Formula (A) and one or more alcohols with an amine catalyst to produce longer-chain ketones from at least a portion of the methyl ketones independently having the structure of Formula (A) and at least a portion of the alcohols.

Provided herein is also a ketone produced by any of the methods described herein. For example, provided herein is ketone obtained by the method of contacting a methyl ketone and an alcohol with an amine catalyst and a metal catalyst. In another embodiment, provided herein is a ketone obtained by contacting a methyl ketone and an alcohol with an amine catalyst and a metal catalyst in the presence of an additional acid. In another embodiment, provided herein is a ketone obtained by contacting a methyl ketone of Formula (A) and an alcohol with a supported amine catalyst and a metal catalyst. The ketone may be any ketone produced by any of the methods described herein. In some embodiments, provided herein is a ketone obtained by contacting acetone, butanol, and ethanol with an amine catalyst and a metal catalyst.

Separation and Recycling

The catalysts used in the methods described herein, including the amine catalyst and/or the metal catalyst, may be recycled. In some embodiments, the amine catalyst and/or the metal catalyst are separated from the product mixture, and then contacted by an additional reactant mixture.

With reference again to FIG. 1, it should be generally understood that one or more steps may be omitted or added to process 100. For example, in some embodiments, amine catalyst 108 and metal catalyst 110 are isolated from the reaction mixture, and then contacted with an additional methyl ketone and alcohol. In other embodiments, amine catalyst 108 is isolated from the reaction mixture, and combined with an additional metal catalyst, an additional methyl ketone, and an additional alcohol. In other embodiments, metal catalyst 110 is isolated from the reaction mixture, and combined with an additional amine catalyst, an additional methyl ketone, and an additional alcohol.

In some embodiments, the amine catalyst and metal catalyst are recycled together, while in other embodiments, they are recycled separately. In yet other embodiments, the amine catalyst is recycled but the metal catalyst is not, while in other embodiments the metal catalyst is recycled while the amine catalyst is not. Any methods known in the art may be used to separate the amine catalyst and/or the metal catalyst from the product mixture. For example, in one embodiment, a supported amine catalyst and a metal catalyst are separated from the product mixture by centrifugation. In another embodiment, a supported amine catalyst is separated from the product mixture by centrifugation, while the metal catalyst is separated from the product mixture by filtration. Separation of the amine catalyst and/or metal catalyst may include multiple steps. For example, in one embodiment, a supported amine catalyst is separated from the product mixture by filtration, then washed with a solvent, and dried.

In other embodiments, the amine catalyst and metal catalyst are contacted by additional reactants without separation from the product mixture. For example, additional fermentation product mixture (e.g., ABE mixture) may be added to the reaction vessel to further increase the overall product yield.

Recycling of the amine catalyst and/or metal catalyst may also include recycling of one or more additional acids. For example, if the amine catalyst is supported on an acidic support, recycling of the amine catalyst could include recycling the acidic support.

Recycling of the amine catalyst and/or metal catalyst may include the addition of one or more new acids. For example, in one embodiment, a supported amine catalyst is separated from a product mixture and a supported acid by distillation, and the separated amine catalyst is combined with a second reactant mixture and a second supported acid to catalyze a second reaction.

Recycling of the amine catalyst and/or metal catalyst may include the addition of one or more new amine catalysts and/or metal catalysts. For example, in one embodiment, a supported amine catalyst is separated from a product mixture and metal catalyst, and the separated amine catalyst is combined with a second reactant mixture and a second metal catalyst to catalyze a second reaction.

The Solvent

In some embodiments, the methods of producing the ketones using an amine catalyst and a metal catalyst as described herein are performed neat, i.e., without addition of a solvent. However, in other embodiments, the methods of producing the ketones using an amine catalyst and a metal catalyst may be performed with a solvent. With reference to FIG. 1, while the use of amine catalyst 108 and metal catalyst 110 is depicted in the absence of solvent, in some variations a solvent may additionally be included in the reaction mixture.

Any solvent that promotes condensation of methyl ketones and alcohols may be employed in the process described herein. For example, the solvent may be an organic solvent. Organic solvents may include aromatics (e.g., toluene, benzene), acetates (e.g., ethyl acetate or isopropylacetate), nitriles (e.g., acetonitrile), or ethers (e.g., diglyme, monoglyme, diglybu, THF). As used herein, "diglyme" refers to diethylene glycol dimethyl ether. As used herein, "diglybu" refers to diethylene glycol dibutyl ether. In some embodiments, the solvent may include toluene, xylenes, dimethylsulfoxide, dimethylformamide, tetrahydrofuran, or $C_6$-$C_{12}$ alkanes. In one embodiment, the solvent includes toluene.

The Reaction Conditions

Reaction Phase

The methyl ketones, alcohols, amine catalysts, metal catalysts, and acids in the methods described herein can be provided in any phase, or mixture of phases, that promotes the condensation of the methyl ketones and alcohols to produce longer-chain ketones. The longer-chain ketones produced may be in any phase. These phases include the gas phase, liquid phase, solid phase, or any combination thereof.

In one embodiment, condensation of a methyl ketone and an alcohol occurs with a gas phase methyl ketone, a gas phase alcohol, a solid phase supported amine catalyst, and a solid phase metal catalyst to produce a gas phase longer-chain ketone. In another embodiment, condensation of a methyl ketone and an alcohol occurs with a liquid phase methyl ketone, a liquid phase alcohol, a solid phase supported amine catalyst, and a solid phase metal catalyst to produce a liquid phase longer-chain ketone. In another embodiment, condensation of a methyl ketone and an alcohol occurs with a gas phase methyl ketone, a gas phase alcohol, a solid phase amine catalyst, a solid phase metal catalyst, and a liquid phase acid to produce a liquid phase longer-chain ketone. In yet another embodiment, condensation of a methyl ketone with more than one alcohol occurs with a liquid phase methyl ketone, liquid phase alcohols, a solid phase supported amine catalyst, and a solid phase supported metal catalyst, to produce a liquid phase longer-chain ketone.

Operating Temperature

The methods described herein may be performed at any suitable temperature to produce the ketones.

The operating temperature range selected may vary depending on various factors, including the solvent, amine catalyst, acid, and metal catalyst. In some embodiments, the operating temperature range is between about 350 K to about 550 K, between about 350 K to about 500 K, or between about 400 K to about 450 K.

In some embodiments, the reaction may be exothermic and inter-stage cooling may be utilized to maintain the temperature at the operating temperature.

Operating Pressure

The operating pressure of the methods described herein to produce the ketones may vary. The operating pressure refers to the pressure across a reaction zone. In some embodiments, the pressure in between 1 atm and 60 atm.

Reaction Time

In some embodiments, the reaction may be carried out for 24 hours, but the time of the reaction will also vary with the reaction conditions (e.g., reaction temperature), catalyst activity, desired yield, and desired conversion (e.g., low conversion with recycle). In some embodiments, the reaction time is determined by the rate of conversion of the starting material. In some embodiments, the reaction mixture is heated for 10 minutes to 30 hours. In other embodiments, the reaction mixture is heated for 10 to 24 hours. In yet other embodiments, the reaction mixture is heated for 18 to 24 hours. In yet other embodiments, the reaction is heated for 1 to 10 hours. In yet other embodiments, the reaction mixture is heated for 10 minutes to 10 hours.

Other Process Considerations

In some embodiments, the reaction is in a batch reactor. In other embodiments, the reaction would is in a flow reactor. In yet other embodiments, the reaction is in a plug flow reactor (PFR), such as a packed bed reactor, as either a single reactor or a multiple tube reactor. In some embodiments, unreacted feedstocks and/or one or more intermediate reaction products are separated from the products downstream of the reactor and recycled back into the reaction zone to be contacted with the amine catalyst.

Provided is a ketone obtained by any of the methods set forth herein. Thus, in one embodiment, provided herein is ketone products (e.g., longer-chain ketones), by contacting a methyl ketone and at least one alcohol with an amine catalyst and a metal catalyst and producing ketone products (e.g., longer-chained ketones) from at least a portion of the methyl ketone and the at least one alcohol by a condensation reaction.

Uses of Ketone Products

The ketones produced by any of the methods described herein may be suitable for use as fuels, gasoline additives, and/or lubricants, and precursors thereof. For example, in some variations, the ketone products containing 5 to 24 carbon atoms are suitable for use in producing fuels. In other variations, the longer-chain ketones containing at least 24 carbon atoms are suitable for use in producing lubricants. In yet other variations, the longer-chain ketones containing 5 to 24 carbon atoms are suitable for use in producing gasoline additives.

Such ketones may be hydrodeoxygenated to produce their corresponding alkanes. Such alkanes may be used as fuels, gasoline additives, or lubricants. One of skill in the art would recognize the suitable catalyst and reactions conditions that may be used to perform the hydrodeoxygenation reaction to produce alkanes. For example, the hydrodeoxygenation catalyst may include Ni, Pt, Pd, Rh, Ru, Cu, and other transition metals. In combination with metals, acidic supports such $NbOPO_4$, $Nb_2O_3$, $SiO_2$—$Al_2O_3$, $Ta_2O_5$, $TiO_2$, $ZrO_2$, and sulfated $ZrO_2$ may also be used to provide hydrogenation activity. One such catalyst is $Pt/NbOPO_4$.

Thus, in some aspects, provided herein are methods to convert the ketone products into alkanes for use as fuels, fuel additives, and/or lubricants.

The ketone(s) produced by the methods described herein may also be reduced (e.g., hydrogenated) to produce their corresponding alcohols. Such alcohols may be used as fuels, gasoline additives, and/or lubricants, or precursors thereof. One of skill in the art would recognize the suitable catalyst and reactions conditions that may be used to perform the reduction reaction. For example, the catalysts described above for hydrodeoxygenation to produce alkanes may also be used to produce alcohols, for example, under milder reaction conditions. Thus, in some aspects, provided herein are methods to convert the longer-chain ketones into alcohols for use as fuels, gasoline additives, and/or lubricants, or precursors thereof.

The hydrodeoxygenation and/or hydrogenating of ketone(s) produced by the methods described herein may also produce a mixture of alkanes and alcohols, suitable for use as fuels, fuel additives, and/or lubricants, or precursors thereof.

Compositions

Provided are also compositions including any of the amine catalysts, any of the metal catalysts, and any of the methyl ketones and alcohols as described herein. The composition may additionally include an acid, which may include any of the acids described herein.

In one variation, provided herein is a composition that includes: a methyl ketone, at least one alcohol, an amine catalyst, and a metal catalyst. In another variation, provided herein is a composition, comprising a methyl ketone, at least two alcohols, an amine catalyst, and a metal catalyst. In yet another variation, provided herein is a composition, comprising a methyl ketone, at least one alcohol, an amine catalyst, a metal catalyst, and an acid. In any of the foregoing compositions, the composition further includes a solvent.

In some embodiments, the additional acid is a supported acid. In other embodiments, the acid is an unsupported acid.

In some embodiments, provided herein is a composition that includes: acetone, butanol, ethanol, a metal catalyst, and an amine catalyst. In some embodiments, the amine catalyst is supported. In one embodiment, the composition includes acetone, butanol, ethanol, palladium supported on silica, and a secondary amine moiety supported on silica-alumina. In other embodiments, provided herein is a composition, comprising acetone, butanol, ethanol, a metal catalyst, an amine catalyst, and a longer-chain ketone obtained by contacting the methyl ketone and the alcohol with the amine catalyst and the metal catalyst.

In any of the foregoing embodiments of the composition, the composition further includes water.

As used herein, "alkyl" refers to a linear or branched saturated hydrocarbon chain. Examples of alkyl groups include methyl, ethyl, n-propyl, iso-propyl, n-butyl, sec-butyl, tert-butyl, n-pentyl, 2-pentyl, iso-pentyl, neo-pentyl, hexyl, 2-hexyl, 3-hexyl, and 3-methylpentyl. When an alkyl residue having a specific number of carbons is named, all geometric isomers having that number of carbons may be encompassed; thus, for example, "butyl" can include n-butyl, sec-butyl, iso-butyl and tert-butyl; "propyl" can include n-propyl and iso-propyl. In some embodiments, alkyl as used herein, such as in compounds of Formula (A), has 1 to 30 carbon atoms (i.e., $C_{1-30}$ alkyl), 1 to 20 carbon atoms (i.e., $C_{1-20}$ alkyl), 1 to 15 carbon atoms (i.e., $C_{1-15}$ alkyl), 1 to 9 carbon atoms (i.e., $C_{1-9}$ alkyl), 1 to 8 carbon atoms (i.e., $C_{1-8}$ alkyl), 1 to 7 carbon atoms (i.e., $C_{1-7}$ alkyl), 1 to 6 carbon atoms (i.e., $C_{1-6}$ alkyl), 1 to 5 carbon atoms (i.e., $C_{1-5}$ alkyl), 1 to 4 carbon atoms (i.e., $C_{1-4}$ alkyl), 1 to 3 carbon atoms (i.e., $C_{1-3}$ alkyl), 1 to 2 carbon atoms (i.e., $C_{1-2}$ alkyl), or 1 carbon atom (i.e., $C_1$ alkyl).

As used herein, "heterocycle" refers to a cyclic compound with one or more ring heteroatoms. In some variations, the heteroatoms are independently selected from nitrogen, oxygen, sulfur, and phosphorous. Heterocycles can include one or more rings, include fused and bridged groups, and can be saturated or have any degree of unsaturation. Examples of heterocycles include, for example, pyrrolidine, piperidine, piperazine, oxetane, dioxolane, azetidine, morpholine, furan, pyrrol, thiophenyl, imidazole, thiazole, pyridazine, pyrimidine, and pyrazole. In some embodiments, heterocycle as used herein, such as in compounds of Formula (A), has 2 to 40 ring carbon atoms (i.e., $C_{2-40}$ heterocycle), 2 to 30 ring carbon atoms (i.e., $C_{2-30}$ heterocycle), 2 to 20 ring carbon atoms (i.e., $C_{2-20}$ heterocycle), 2 to 15 ring carbon atoms (i.e., $C_{2-15}$ heterocycle), 2 to 12 ring carbon atoms (i.e., $C_{2-12}$ heterocycle), 2 to 10 ring carbon atoms (i.e., $C_{2-10}$ heterocycle), or 2 to 8 ring carbon atoms (i.e., $C_{2-8}$ heterocycle); and 1 to 8 ring heteroatoms, 1 to 6 ring heteroatoms, 1 to 4 ring heteroatoms, 1 to 3 ring heteroatoms, 1 or 2 ring heteroatoms, or 1 ring heteroatom independently selected from nitrogen, sulfur, oxygen, or phosphorous. "Heterocyclyl" refers to the radical moiety of the equivalent heterocycle. An example of a heterocyclyl is piperidinyl, corresponding to the radical moiety of the heterocycle piperidine.

As used herein, "carbocycle" refers to a cyclic compound in which all the ring atoms are carbon atoms. Carbocycles can include one or more rings, including fused and bridged groups, and can be saturated or have any degree of unsaturation. Carbocycles may include, for example, cycloalkyl compounds and aryl compounds. Examples of carbocycles include, for example, benzene, naphthalene, anthracine, cyclopropane, cyclobutane, cyclopentane, cyclohexane, cyclopentene, and cyclohexene. In some embodiments, carbocycle as used herein, such as in compounds of Formula (A), has 2 to 40 ring carbon atoms (i.e., $C_{2-40}$ carbocycle), 2 to 30 ring carbon atoms (i.e., $C_{2-30}$ carbocycle), 2 to 20 ring carbon atoms (i.e., $C_{2-20}$ carbocycle), 2 to 15 ring carbon atoms (i.e., $C_{2-15}$ carbocycle), 2 to 12 ring carbon atoms (i.e., $C_{2-12}$ carbocycle), 2 to 10 ring carbon atoms (i.e., $C_{2-10}$ carbocycle), or 2 to 8 ring carbon atoms (i.e., $C_{2-8}$ carbocycle). "Carbocyclyl" refers to the radical moiety of the equivalent carbocycle. An example of a carbocyclyl is cyclohexyl, corresponding to the radical moiety of the carbocycle cyclohexane.

As used herein, "ether" refers to —R—O—R', wherein R and R' are independently alkyl, carbocycle, or hetereocycle. Examples of ethers include dimethyl ether, diethyl ether, methyl ethyl ether, and methyl tert-butyl ether. A substituted ether may be formed by replacing one or more hydrogen atoms on the R or R' with a moiety other than hydrogen, provided that the designated atom's normal valence is not exceeded.

As used herein, "thioether" refers to —R—S—R', wherein R and R' are independently alkyl, carbocycle, or hetereocycle. Examples of thioethers include dimethyl thioether, diethyl thioether, methyl ethyl thioether, and methyl tert-butyl thioether. A substituted thioether may be formed by replacing one or more hydrogen atoms on the R or R' with a moiety other than hydrogen, provided that the designated atom's normal valence is not exceeded.

The term "substituted", as used herein, means that any one or more hydrogen atoms on the designated atom or group is replaced with a moiety other than hydrogen, provided that the designated atom's normal valence is not exceeded.

It should be understood that when a range of values is listed, it is intended to encompass each value and sub-range within the range. For example, "$C_{1-6}$ alkyl" (which may also be referred to as 1-6C alkyl, C1-C6 alkyl, or C1-6 alkyl) is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

It should be understood that reference to "between" two values or parameters herein includes (and describes) embodiments that include those two values or parameters per se. For example, description referring to "between x and y" includes description of "x" and "y" per se.

ENUMERATED EMBODIMENTS

The following enumerated embodiments are representative of some aspects of the invention.

1. A method of producing a ketone mixture, comprising contacting a methyl ketone and at least one alcohol with: (a) a catalyst comprising an amine moiety and a metal moiety; or (b) an amine catalyst and a metal catalyst, to produce a ketone mixture by condensation of the methyl ketone and the at least one alcohol, wherein: the methyl ketone has the structure of Formula (A):

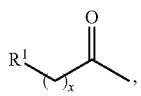

(A)

wherein:
   $R^1$ is H, alkyl, carbocyclyl, or heterocyclyl;
      wherein the alkyl, carbocyclyl, or heterocyclyl is unsubstituted or substituted with one or more substituents independently selected from the group consisting of hydroxyl, nitro, and halo; and
   x is an integer greater than or equal to 1.
2. The method of embodiment 1, wherein the at least one alcohol is a primary alcohol.
3. The method of embodiment 1 or 2, wherein the contacting of the methyl ketone of Formula (A) and the at least one alcohol with (a) the catalyst comprising the amine moiety and the metal moiety; or (b) the amine catalyst and the metal catalyst, forms an enamine complex.
4. The method of any one of embodiments 1 to 3, wherein: water is present at a concentration between 1 mole % and 20 mole %; and the % yield of the ketone mixture produced decreases less than 20% over 16 hours.
5. The method of any one of embodiments 1 to 4, wherein the methyl ketone and the at least one alcohol are provided in a fermentation product mixture.
6. The method of any one of embodiments 1 to 5, further comprising contacting a composition comprising biomass or sugars with a fermentation host to produce a fermentation product mixture, wherein the fermentation product mixture comprises the methyl ketone and the at least one alcohol.
7. The method of embodiment 6, wherein the fermentation host is selected from the group consisting of fungi and bacteria.
8. The method of any one of embodiments 1 to 7, further comprising:
   isolating the amine catalyst from the ketone mixture produced to obtain an isolated amine catalyst.
9. The method of embodiment 8, further comprising:
   contacting an additional methyl ketone and at least one additional alcohol with the isolated amine catalyst and a metal catalyst; and
   producing an additional ketone mixture.
10. The method of any one of embodiments 1 to 9, further comprising:
    isolating the metal catalyst from the ketone mixture produced to obtain an isolated metal catalyst.
11. The method of embodiment 10, further comprising:
    contacting an additional methyl ketone and at least one additional alcohol with the isolated metal catalyst and an amine catalyst; and
    producing an additional ketone mixture.
12. A method of producing a ketone mixture, comprising:
    contacting a composition comprising biomass or sugars with a fermentation host to produce a fermentation product mixture, wherein the fermentation product mixture comprises acetone, butanol and ethanol;
    contacting the acetone, butanol and ethanol with an amine catalyst and a metal catalyst to produce a ketone mixture.
13. The method of embodiment 12, wherein at least a portion of the ketone mixture produced is by double alkylation of the acetone.
14. The method of any one of embodiments 1 to 13, wherein at least 15% of the ketone mixture produced is $C_{7+}$ hydrocarbon ketones.
15. The method of any one of embodiments 1 to 14, wherein at least 25% of the ketone mixture produced is $C_{5+}$ hydrocarbon ketones.
16. The method of any one of embodiments 1 to 15, wherein the amine catalyst comprises an amine moiety having the structure:

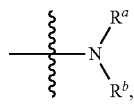

wherein $R^a$ and $R^b$ at each occurrence are independently H, alkyl, carbocyclyl, heterocyclyl, ether, or any combinations thereof;
   wherein the alkyl, carbocyclyl, heterocyclyl, or ether is independently unsubstituted or substituted with one or more substituents selected from the group consisting of alkyl, hydroxyl, amine, oxo, carboxyl, imine, carbocyclyl, heterocyclyl, halo, ether, and thioether;
   or $R^a$ and $R^b$ are taken together with the nitrogen atom to which they are both attached to form a heterocycle,
      wherein the heterocycle is unsubstituted or substituted with one or more substituents selected from the group consisting of alkyl, hydroxyl, amine, oxo, carboxyl, imine, carbocyclyl, heterocyclyl, halo, ether, and thioether.
17. The method of embodiment 16, wherein $R^a$ and $R^b$ are taken together with the nitrogen atom to which they are both attached to form a heterocycle, wherein the heterocycle comprises:

1 to 8 heteroatoms;
wherein the heteroatoms are independently selected from the group consisting of N, O, S, and P;
1 to 30 carbon ring atoms; and
the heterocycle is unsubstituted or substituted with one or more substituents selected from the group consisting of alkyl, hydroxyl, amine, oxo, carboxyl, imine, carbocyclyl, heterocyclyl, halo, ether, and thioether.

18. The method of any one of embodiments 1 to 15, wherein the amine catalyst comprises an amine moiety, wherein the amine moiety comprises a heterocycle containing at least one nitrogen atom, wherein the heterocycle is unsubstituted or substituted with one or more substituents selected from the group consisting of alkyl, carbocyclyl, heterocyclyl, carboxyl, hydroxyl, halo, ether, and thioether.

19. The method of embodiment 18, wherein the heterocycle comprises 1 to 30 carbon atoms and 1 to 8 heteroatoms, wherein the heteroatoms are independently selected from the group consisting of N, O, S, and P.

20. The method of any one of embodiments 1 to 29, wherein the amine catalyst further comprises a solid support and a linker, wherein the linker attaches the amine moiety to the solid support.

21. The method of embodiment 20, wherein the solid support comprises silica, alumina, silica-alumina, TiO$_2$, ZrO$_2$, or Nb$_2$O$_5$, or any combinations thereof.

22. The method of embodiment 20 or 21, wherein the solid support comprises silica-alumina.

23. The method of any one of embodiments 20 to 22, wherein the solid support is porous.

24. The method of any one of embodiments 20 to 23, wherein the solid support comprises a plurality of pores, wherein at least a portion of the pores have a pore diameter between 2 nm and 50 nm.

25. The method of embodiment 24, wherein the pore diameter is between 2 nm and 40 nm.

26. The method of embodiment 24 or 25, wherein the pore diameter is between 2 nm and 30 nm.

27. The method of any one of embodiments 20 to 26, wherein the solid support comprises a mesoporous silica selected from the group consisting of MCM-41, SBA-15, and KIT-6.

28. The method of any one of embodiments 20 to 27, wherein the solid support comprises an acid moiety.

29. The method of embodiment 28, wherein the acid moiety is selected from the group consisting of carboxylic, phosphoric, and sulfonic, or any combinations thereof.

30. The method of any one of embodiments 20 to 29, wherein the solid support comprises silicon, aluminum, germanium, boron, or phosphorous atoms, or any combinations thereof.

31. The method of any one of embodiments 20 to 30, wherein the solid support comprises a moiety having a structure of formula M-Y—Z, wherein:
M is silica, alumina, silica-alumina, TiO$_2$, ZrO$_2$, Nb$_2$O$_5$, or any combinations thereof;
Y is silicon, aluminum, germanium, boron, or phosphorous; and
Z is a linker connecting Y and the amine moiety.

32. The method of any one of embodiments 20 to 31, wherein the linker comprises:
-alkyl-, -aliphatic-, -aryl-, -carbocycle-, -heterocycle-, -sulfone-, -ether-, or any combinations thereof;
wherein the -alkyl-, -aliphatic-, -aryl-, -carbocycle-, -heterocycle-, -sulfone-, -ether- are unsubstituted or substituted with one or more substituents independently selected from the group consisting of alkyl, hydroxyl, amine, oxo, carboxyl, imine, carbocyclyl, and heterocyclyl.

33. The method of any one of embodiments 20 to 32, wherein the linker comprises at least three linear chain atoms.

34. The method of any one of embodiments 20 to 33, wherein the linker comprises 3 to 30 linear chain atoms.

35. The method of any one of embodiments 20 to 34, wherein the linker comprises 3 to 20 linear chain atoms.

36. The method of any one of embodiments 1 to 35, wherein the amine catalyst comprises a secondary amine.

37. The method of any one of embodiment 19 to 35, wherein the amine moiety is selected from the group consisting of:

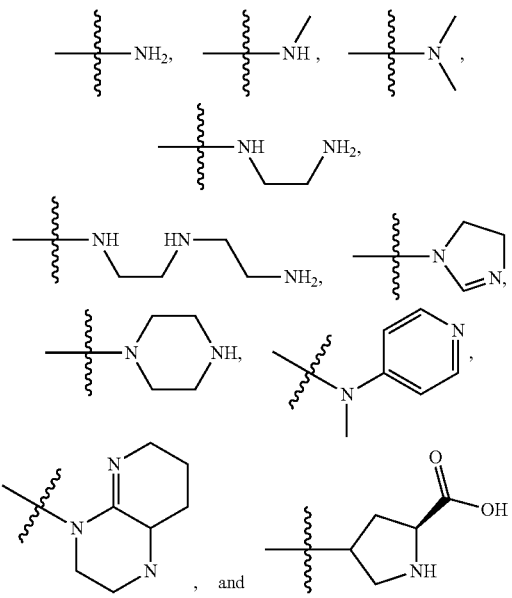

38. The method of any one of embodiments 1 to 35, or 37, wherein the amine catalyst comprises:

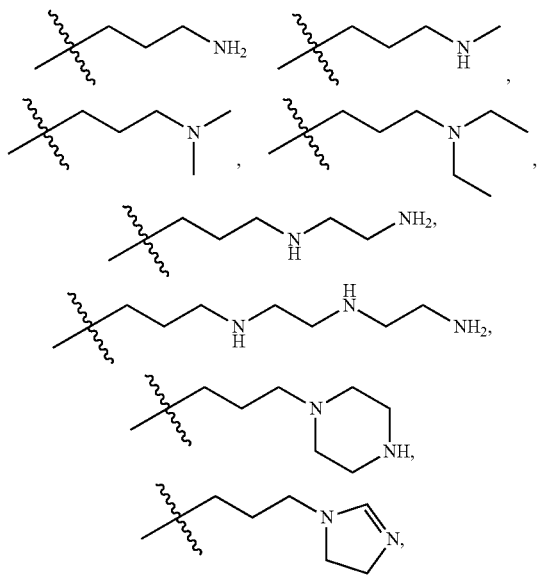

-continued

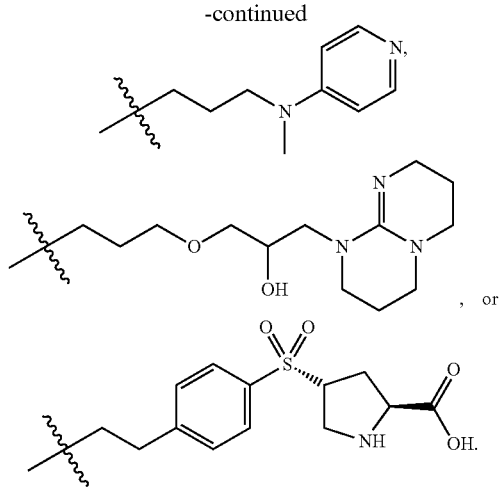

39. The method of any one of embodiments 20 to 38, wherein the linker comprises:

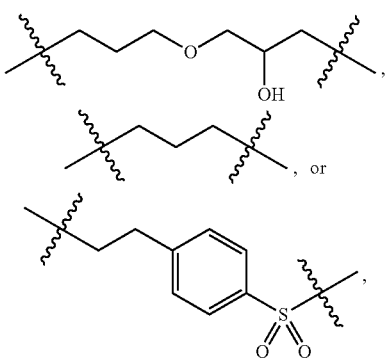

40. The method of any one of embodiments 1 to 11, or 14 to 39, wherein the methyl ketone and the at least one alcohol are contacted with the amine catalyst and the metal catalyst in the presence of an acid.
41. The method of embodiment 40, wherein the acid is supported or unsupported.
42. The method of embodiment 40 or 41, wherein the acid is supported on a support comprising silica, silica-alumina, alumina, $TiO_2$, $ZrO_2$, $Nb_2O_5$, or any combinations thereof.
43. The method of embodiment 40 or 41, wherein the acid is selected from the group consisting of acetic acid, benzoic acid, terephthalic acid, phthalic acid, isophthalic acid, adipic acid, succinic acid, oxalic acid, pimelic acid, valeric acid, muconic acid, mucic acid, toluic acid, citric acid, and mineral acids, or any combinations thereof.
44. The method of any one of embodiments 40 to 43, wherein the acid comprises a carboxylic acid moiety.
45. The method of embodiment 40 or 41, wherein the acid is selected from the group consisting of acetic acid and benzoic acid.
46. The method of any one of embodiments 1 to 11, or 14 to 45, wherein the methyl ketone of Formula (A), the at least one alcohol, the amine catalyst, and the metal catalyst are further contacted by a solvent.
47. The method of embodiment 47, wherein the solvent comprises toluene, xylenes, dimethyl sulfoxide, dimethylfuran, tetrahydrofuran, alkanes, or any combination thereof.
48. The method of embodiment 46 or 47, wherein the solvent comprises toluene.
49. The method of any one of embodiments 1 to 11, or 14 to 48, wherein the methyl ketone of Formula (A) and the at least one alcohol are contacted with the amine catalyst and the metal catalyst at an operating temperature range from 350 to 550 K.
50. The method of any one of embodiments 1 to 11, or 14 to 49, wherein x is an integer from 1 to 30.
51. The method of any one of embodiments 1 to 50, wherein the metal catalyst is palladium on alumina.
52. The method of any one of embodiments 1 to 11, or 14 to 51, wherein the at least one alcohol is selected from the group consisting of butanol and ethanol.
53. A method, comprising:
producing a ketone mixture according to the method of any one of embodiments 1 to 52; and
hydrodeoxygenating the ketone mixture to produce an alkane from at least a portion of the ketone mixture.
54. A method, comprising:
producing a ketone mixture according to the method of any one of embodiments 1 to 52; and
reducing the ketone mixture to produce an alcohol from at least a portion of the ketone mixture.
55. A ketone produced according to any one of the methods of embodiments 1 to 52.
56. An alkane produced according to the method of embodiment 53.
57. An alcohol produced according to the method of embodiment 54.
58. A composition, comprising:
a fossil fuel; and
an alkane of embodiment 56, an alcohol of embodiment 57, or mixture thereof.
59. A composition, comprising a methyl ketone, at least one alcohol, an amine catalyst, and a metal catalyst, wherein:
the methyl ketone has the structure of Formula (A):

wherein:
$R^1$ is H, alkyl, carbocyclyl, or heterocyclyl;
wherein the alkyl, carbocyclyl, or heterocyclyl is unsubstituted or substituted with one or more substituents independently selected from the group consisting of hydroxyl, nitro, and halo; and
x is an integer greater than or equal to 1.
60. The composition of embodiment 59, further comprising a product ketone mixture.
61. The composition of embodiment 59 or 60, wherein the at least one alcohol is a primary alcohol.
62. The composition of embodiment 61, wherein at least 15% of the product ketone mixture comprises one or more $C_{7+}$ hydrocarbon ketones.
63. The composition of embodiment 61 or 62, wherein at least 25% of the product ketone mixture comprises one or more $C_{5+}$ hydrocarbon ketones.
64. The composition of any one of embodiments 59 to 63, wherein the amine catalyst comprises an amine moiety having the structure:

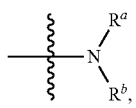

wherein $R^a$ and $R^b$ at each occurrence are independently H, alkyl, carbocyclyl, heterocyclyl, or ether, or any combinations thereof;
  wherein the alkyl, carbocyclyl, heterocyclyl, or ether is independently unsubstituted or substituted with one or more substituents selected from the group consisting of alkyl, hydroxyl, amine, oxo, carboxyl, imine, carbocyclyl, heterocyclyl, halo, ether, and thioether;
  or $R^a$ and $R^b$ are taken together with the nitrogen atom to which they are both attached to form a heterocycle,
    wherein the heterocycle is unsubstituted or substituted with one or more substituents selected from the group consisting of alkyl, hydroxyl, amine, oxo, carboxyl, imine, carbocyclyl, heterocyclyl, halo, ether, and thioether.

65. The composition of embodiment 64, wherein $R^a$ and $R^b$ are taken together with the nitrogen atom to which they are both attached to form a heterocycle, wherein the heterocycle comprises:
  1 to 8 heteroatoms;
  wherein the heteroatoms are independently selected from the group consisting of N, O, S, and P;
  1 to 30 carbon ring atoms; and
  the heterocycle is unsubstituted or substituted with one or more substituents selected from the group consisting of alkyl, hydroxyl, amine, oxo, carboxyl, imine, carbocyclyl, heterocyclyl, halo, ether, and thioether.

66. The composition of any one of embodiments 59 to 63, wherein the amine catalyst comprises an amine moiety, wherein the amine moiety comprises a heterocycle containing at least one nitrogen atom, wherein the heterocycle is unsubstituted or substituted with one or more substituents selected from the group consisting of alkyl, carbocyclyl, heterocyclyl, carboxyl, hydroxyl, halo, ether, and thioether.

67. The composition of embodiment 66, wherein the heterocycle comprises 1 to 30 carbon atoms and 1 to 8 heteroatoms, wherein the heteroatoms are independently selected from the group consisting of N, O, S, and P.

68. The composition of any one of embodiments 59 to 67, wherein the amine catalyst further comprises a solid support and a linker, wherein the linker attaches the amine moiety to the solid support.

69. The composition of embodiment 68, wherein the solid support comprises silica, alumina, silica-alumina, $TiO_2$, $ZrO_2$, or $Nb_2O_5$, or any combinations thereof.

70. The composition of embodiment 68 or 69, wherein the solid support comprises silica-alumina.

71. The composition of any one of embodiments 68 to 70, wherein the solid support is porous.

72. The composition of any one of embodiments 68 to 71, wherein the solid support comprises a plurality of pores, wherein at least a portion of the pores have a pore diameter between 2 nm and 50 nm.

73. The composition of embodiment 72, wherein the pore diameter is between 2 nm and 40 nm.

74. The composition of embodiment 72 or 73, wherein the pore diameter is between 2 nm and 30 nm.

75. The composition of any one of embodiments 68 to 74, wherein the solid support comprises a mesoporous silica selected from the group consisting of MCM-41, SBA-15, and KIT-6.

76. The composition of any one of embodiments 68 to 75, wherein the solid support comprises an acid moiety.

77. The composition of embodiment 76, wherein the acid moiety is selected from the group consisting of carboxylic, phosphoric, and sulfonic, or any combinations thereof.

78. The composition of any one of embodiments 68 to 77, wherein the solid support comprises silicon, aluminum, germanium, boron, or phosphorous atoms, or any combinations thereof.

79. The composition of any one of embodiments 68 to 78, wherein the solid support comprises a moiety having a structure of formula M-Y—Z, wherein:
  M is silica, alumina, silica-alumina, $TiO_2$, $ZrO_2$, $Nb_2O_5$, or any combinations thereof;
  Y is silicon, aluminum, germanium, boron, or phosphorous; and
  Z is a linker connecting Y and the amine moiety.

80. The composition of any one of embodiments 68 to 79, wherein the linker comprises:
  -alkyl-, -aliphatic-, -aryl-, -carbocycle-, -heterocycle-, -sulfone-, or -ether-, or any combinations thereof;
  wherein the -alkyl-, -aliphatic-, -aryl-, -carbocycle-, -heterocycle-, -sulfone-, -ether- are unsubstituted or substituted with one or more substituents independently selected from the group consisting of alkyl, hydroxyl, amine, oxo, carboxyl, imine, carbocyclyl, and heterocyclyl.

81. The composition of any one of embodiments 68 to 80, wherein the linker comprises at least three linear chain atoms.

82. The composition of any one of embodiments 68 to 81, wherein the linker comprises 3 to 30 linear chain atoms.

83. The composition of any one of embodiments 68 to 82, wherein the linker comprises 3 to 20 linear chain atoms.

84. The composition of any one of embodiments 59 to 83, wherein the amine catalyst comprises a secondary amine.

85. The composition of any one of embodiment 59 to 83, wherein the amine moiety is selected from the group consisting of:

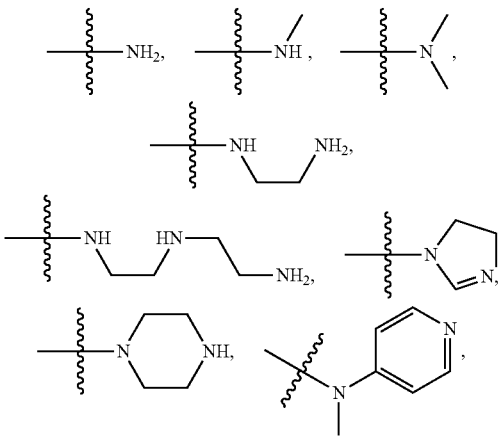

-continued

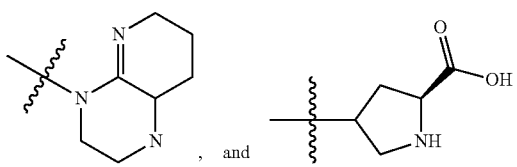, and

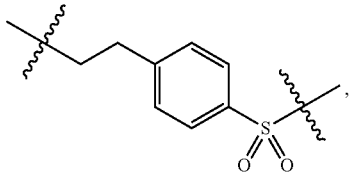,

86. The composition of any one of embodiments 59 to 83, or 85, wherein the amine catalyst comprises:

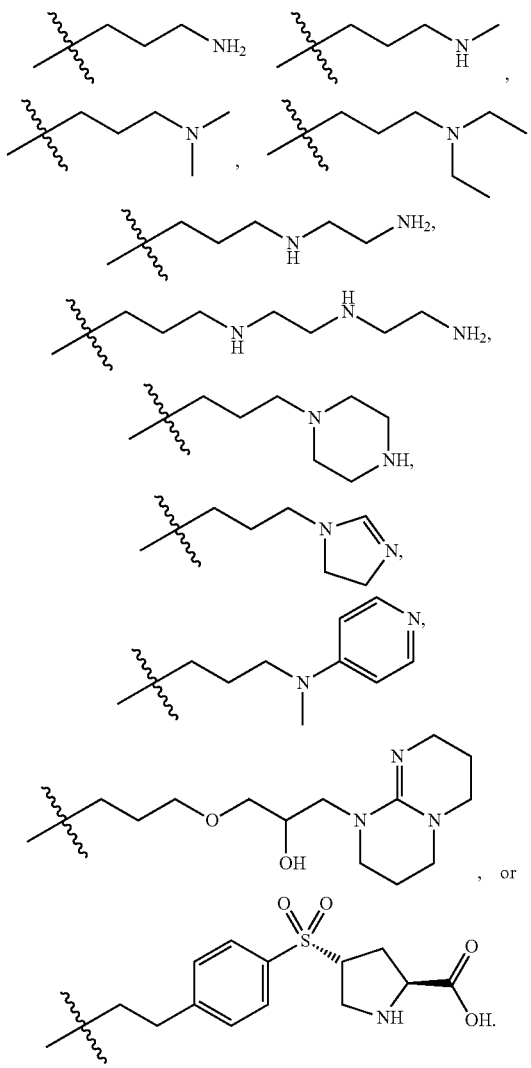

87. The composition of any one of embodiments 59 to 83, wherein the linker comprises:

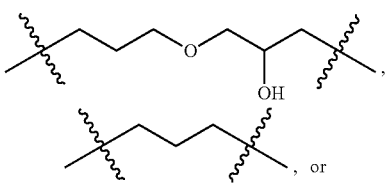

88. The composition of any one of embodiments 59 to 87, further comprising an acid.
89. The composition of embodiment 88, wherein the acid is supported or unsupported.
90. The composition of embodiment 88 or 89, wherein the acid is supported on a support comprising silica, silica-alumina, alumina, $TiO_2$, $ZrO_2$, $Nb_2O_5$, or any combinations thereof.
91. The composition of embodiment 88 or 89, wherein the acid is selected from the group consisting of acetic acid, benzoic acid, terephthalic acid, phthalic acid, isophthalic acid, adipic acid, succinic acid, oxalic acid, pimelic acid, valeric acid, muconic acid, mucic acid, toluic acid, citric acid, and mineral acids, or any combinations thereof.
92. The composition of any one of embodiments 88 to 91, wherein the acid comprises a carboxylic acid moiety.
93. The composition embodiment 88 or 89, wherein the acid is selected from the group consisting of acetic acid and benzoic acid.
94. The composition of any one of embodiments 59 to 93, further comprising a solvent.
95. The composition of embodiment 94, wherein the solvent comprises toluene, xylenes, dimethyl sulfoxide, dimethylfuran, tetrahydrofuran, alkanes, or any combination thereof.
96. The composition of embodiment 94 or 95, wherein the solvent comprises toluene.
97. The composition of any one of embodiments 59 to 96, wherein x is an integer from 1 to 30.
98. The composition of any one of embodiments 59 to 97, wherein the metal catalyst is palladium on alumina.
99. The composition of any one of embodiments 59 to 98, wherein the at least one alcohol is selected from the group consisting of butanol and ethanol.
100. The composition of any one of embodiments 59 to 99, further comprising a fermentation product mixture.
101. The composition, comprising a fermentation product mixture, an amine catalyst, and a metal catalyst, wherein the fermentation product mixture comprises a methyl ketone, at least one alcohol, and water.
102. A fuel or a lubricant, comprising:
   at least one alkane produced according to the method of embodiment 53, or at least one alcohol produced according to the method of embodiment 54, or a mixture thereof.

EXAMPLES

The following Examples are merely illustrative and are not meant to limit any aspects of the present disclosure in any way.

Unless otherwise specified, silica-alumina (BET=470 $m^2g^{-1}$, average pore diameter: ~8 nm), silica (surface area: 500 $m^2g^{-1}$, average pore diameter: ~6 nm), and other chemicals used in the Examples described herein were purchased from either Sigma-Aldrich or Gelest, Inc. and used as received without further purification.

Example 1

Preparation and Characterization of Silica-Alumina Supported Amine Catalysts This Example demonstrates the preparation and characterization of the silica-alumina supported amine catalysts listed in Table 1.

imidazolyl (e.g., Entries 1 to 5, 7). Silica-alumina (Si—Al) support material was calcined in air at 773 K for 6 h and then stored in vacuum prior to use. Typically, the post grafting of organoamines onto Si—Al was accomplished by stirring 1 g of Si—Al using an amine reagent (~1-4 mmol) in 100 ml of ethanol at 343 K for 16 h under inert conditions. The hot solution was then cooled down to room temperature, filtered, washed with copious amounts of ethanol, and then dried in

TABLE 1

| Entry | Catalyst Name | Amine Moiety |
|---|---|---|
| 1 | Si—Al—NH$_2$ | propyl-NH$_2$ |
| 2 | Si—Al—NHR | propyl-NH-CH$_3$ |
| 3 | Si—Al—NR$_2$ | propyl-N(CH$_3$)$_2$ |
| 4 | Si—Al—NEt—NH$_2$ | propyl-NH-CH$_2$CH$_2$-NH$_2$ |
| 5 | Si—Al—(NEt)$_2$—NH$_2$ | propyl-NH-CH$_2$CH$_2$-NH-CH$_2$CH$_2$-NH$_2$ |
| 6 | Si—Al—Piperazine | propyl-piperazine-NH |
| 7 | Si—Al—Imidazole | propyl-imidazole |
| 8 | Si—Al—DMAP | propyl-N(CH$_3$)-(4-pyridyl) |
| 9 | Si—Al—TBD | propyl-O-CH$_2$-CH(OH)-CH$_2$-TBD |
| 10 | Si—Al—Proline | ethyl-phenyl-SO$_2$-(4-pyrrolidinyl-2-CO$_2$H) |

Preparation of Si—Al Supported Catalysts: The following procedure provides a method that can be employed to prepare supported amine catalysts of formula Si—Al—NR'R", wherein R' and R" are independently H, alkyl or vacuum oven at 373 K for overnight. The choice of amine reagent used in the grafting step described above determines the linker length and the amine moiety of the resulting supported amine catalyst. For example, to prepare the supported amine catalyst Entry 1, the calcined Si—Al is stirred with 3-aminopropyltrimethoxysilane. To prepare the supported amine catalyst Entry 2, the calcined Si—Al is stirred with 3-(N-methylaminopropyl)trimethoxysilane.

Preparation of Si—Al Supported Piperazine Catalysts (e.g., Entry 6): 2 g of vacuum dried Si—Al support was allowed to react with (3-chloropropyl)triethoxysilane (4 mmol) in dry toluene at reflux for 24 h. The chloropropylated Si—Al support (1.0 g) was allowed to react with piperazine (~2 mmol) and sodium hydride (4.5 mmol) in 30 mL of dry THF under $N_2$ atmosphere at 0° C. The solution was stirred for additional 1 h at room temperature and the solution was stirred further for 16 h at 70° C. The solution was then filtered, washed with copious amounts of THF and ethanol and dried in vacuo, to give the supported piperazine catalyst Entry 6. Other supported piperazine catalysts can be prepared using this procedure by replacing the (3-chloropropyl)triethoxysilane with an appropriate compound. For example, to prepare a supported a piperazine catalyst with a longer linker, the (3-chloropropyl)triethoxysilane could be substituted with (3-chlorobutyl)triethoxysilane.

Preparation of Si—Al Supported 4-(Dimethylaminopyridine) (DMAP) Catalysts (e.g., Entry 8): 4-(N-methylamino) pyridine (~2 mmol) in 70 mL of dry tetrahydrofuran (THF) was added drop wise to a suspension of sodium hydride (4.5 mmol) in 30 mL of dry THF under $N_2$ atmosphere at 0° C. The solution was stirred for additional 2 h at room temperature. Afterwards, 1 g of chloropropylated Si—Al support containing was slowly added into the reaction mixture and the solution was stirred further for 16 h at 70° C. The solution was then filtered, washed with copious amounts of THF and ethanol and dried in vacuo, to give supported DMAP catalyst Entry 8. Other supported DMAP catalysts can be prepared using this procedure by replacing the (3-chloropropyl)triethoxysilane with an appropriate compound. For example, to prepare a supported a DMAP catalyst with a longer linker, the (3-chloropropyl)triethoxysilane could be substituted with (3-chlorobutyl)triethoxysilane.

Preparation of Si—Al Supported Triazabicyclodecene (TBD) Catalyst (e.g., Entry 9): 2 g of vacuum dried Si—Al support was allowed to react with (3-glycidoxypropyl) trimethoxysilane (4 mmol) in dry toluene at reflux for 24 h. The glycidylated Si—Al support (1.0 g) was allowed to react with 1,5,7-triazabicyclo[4.4.0]undec-3-ene (TBD, ~2 mmol) in toluene (30 mL) at 300 K for 15 h, and excess TBD was removed by soxhlet extraction with dichloromethane and the catalyst was stored under vacuum. Other supported TBD catalysts can be prepared using this procedure by replacing the (3-glycidoxypropyl)trimethoxysilane with an appropriate compound. For example, to prepare a supported a TBD catalyst with a longer linker, the (3-glycidoxypropyl) trimethoxysilane could be substituted with (3-glycidoxybutyl)trimethoxysilane.

Preparation of Si—Al Supported Proline Catalysts (e.g., Entry 10): 3 g of vacuum dried Si—Al support was allowed to react with 4-[2-(trimethoxysilyl)ethyl]benzene-1-sulfonyl chloride (3 mmol) in dry toluene at reflux for 12 h. The —$SO_2Cl$ containing Si—Al support (1.0 g) was allowed to react with the dropwise addition of trans-4-hydroxy-L-proline (~2 mmol) at 60° C., under stirring and the mixture was stirred at 60° C. for 3 h under $N_2$. The solid supported proline catalyst was separated, washed with ethanol, diethyl ether and finally dried under reduced pressure.

Infrared Characterization:

Infrared spectra were acquired using a Thermo Scientific Nicolet 6700 FTIR spectrometer equipped with a liquid nitrogen cooled MCT detector. Each spectrum was obtained by averaging 32 scans taken with 1 $cm^{-1}$ resolution. A 0.05 g portion of Si—Al-supported amine was pressed into a 20 mm-diameter pellet (<1 mm thick) and placed into a custom-built transmission cell equipped with $CaF_2$ windows, a K-type thermocouple for temperature control, and resistive cartridge heaters.

Nuclear Magnetic Resonance (NMR) Characterization: Solid-state $^{13}C$ CP MAS NMR and $^{29}Si$ MAS NMR experiments were performed on a Bruker Avance I 500 MHz spectrometer equipped with a H/X double resonance magic angle spinning probe which uses 4 mm O.D. rotors. $^{13}C$ cross-polarization, tuned to 125.79 MHz, MAS NMR experiments were obtained using a $^1H$ 90° pulse width of 4.2 µs, 2 ms contact time, 60 kHz decoupling field and 2-5 s recycle delay at a spinning rate of 7-13 kHz. All $^{13}C$ spectra were referenced against the chemical shifts of adamantane at 38.48 and 29.45 ppm. The $^{29}Si$ with $^1H$ decoupling MAS NMR spectra were acquired at 99.37 MHz, using a $^{29}Si$ 90° pulse width of 7.5 µs, recycle delay of 600 s, and spinning rate of 10-11 kHz. All $^{29}Si$ spectra were referenced against polydimethylsiloxane at −22 ppm (relative to TMS at 0 ppm). The resolution obtained in the $^{29}Si$ NMR spectra was sufficient for accurate peak assignments, and the relative peak area of each site was obtained by the curve-fitting, using a series of Gaussian peaks.

Figure 2A:
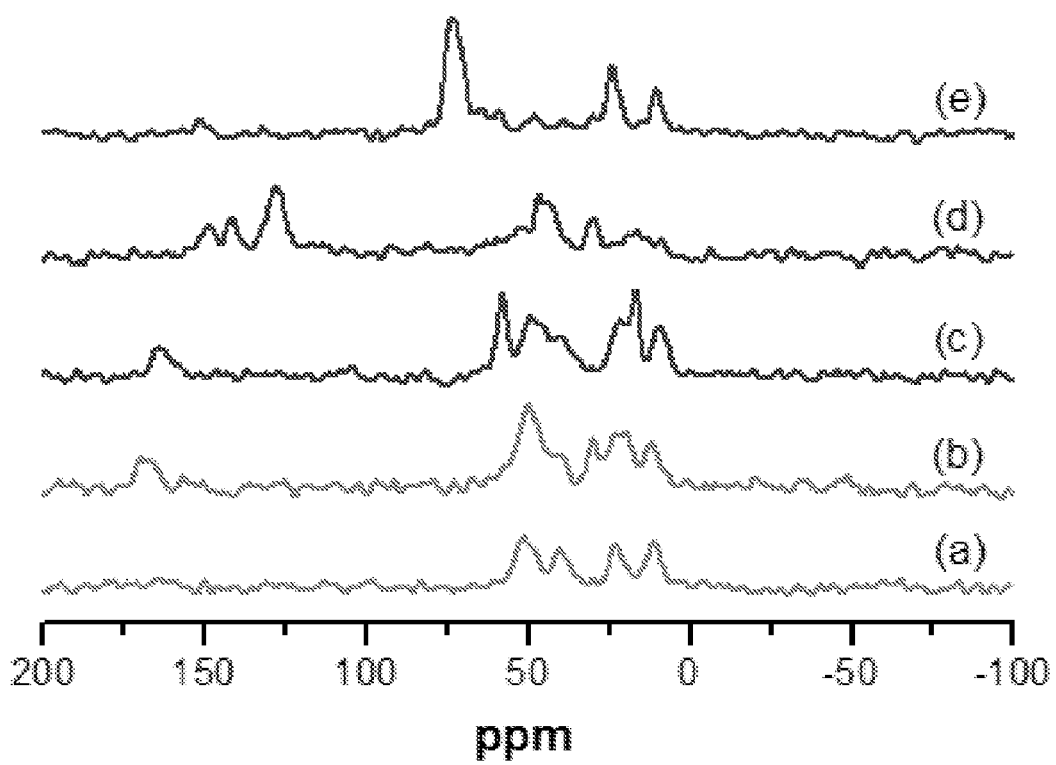
FIG. 2A depicts solid-state $^{13}$C CP magic-angle spinning (MAS) nuclear magnetic resonance (NMR) spectra of silica-alumina supported amine catalysts, wherein the catalyst includes (a) —NHCH$_2$CH$_2$NH$_2$, (b) —(NHCH$_2$CH$_2$)$_2$NH$_2$, (c) imidazole moiety, (d) piperazine moiety, or (e) triazabicyclodecene moiety.
Figure 2B:
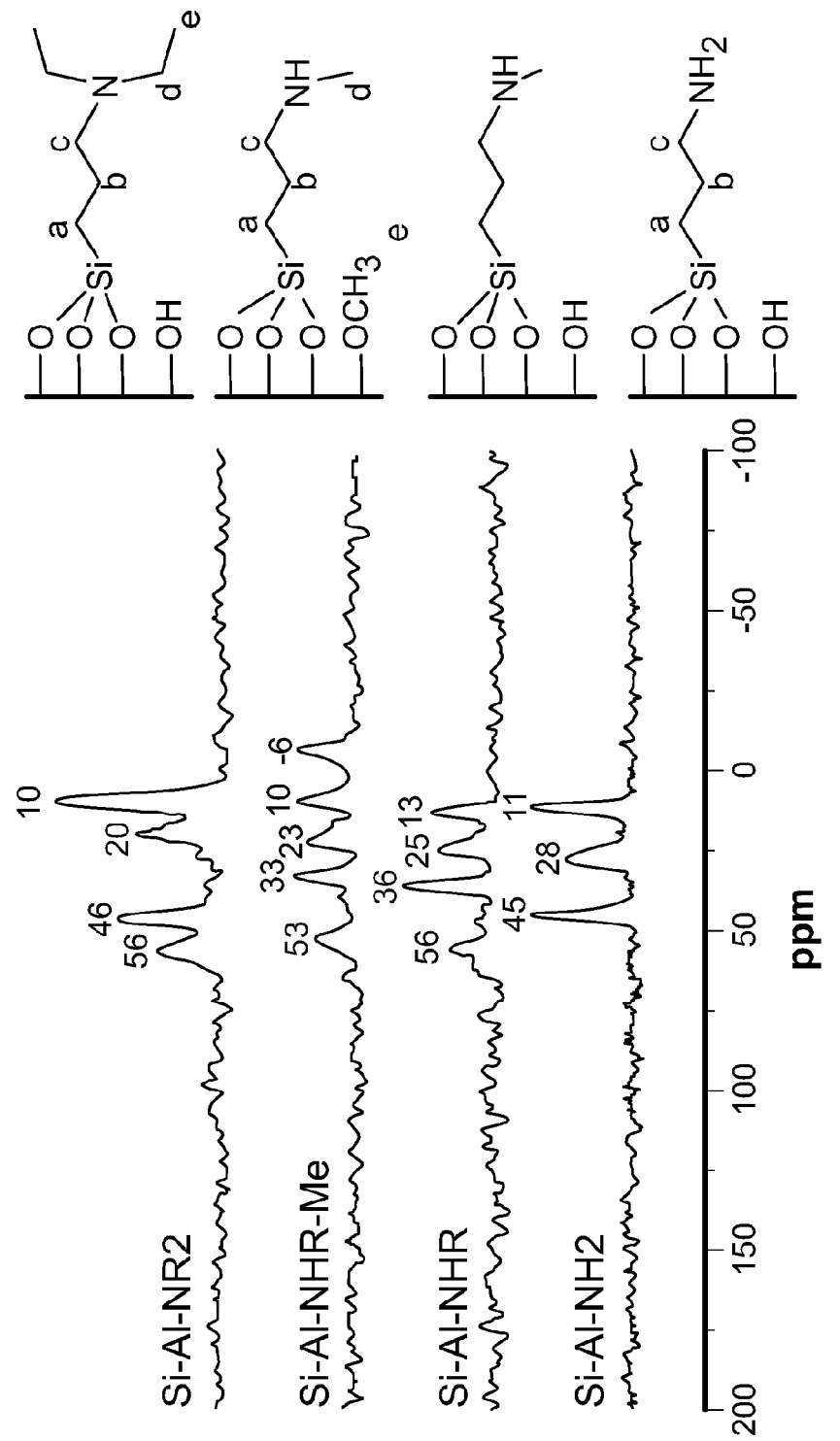
FIG. 2B depicts solid-state $^{13}$C CP MAS NMR spectra of silica-alumina supported amine catalysts, wherein the numbers above the spectra refer to the approximate spectral shift of the corresponding peaks.
Figure 3A:
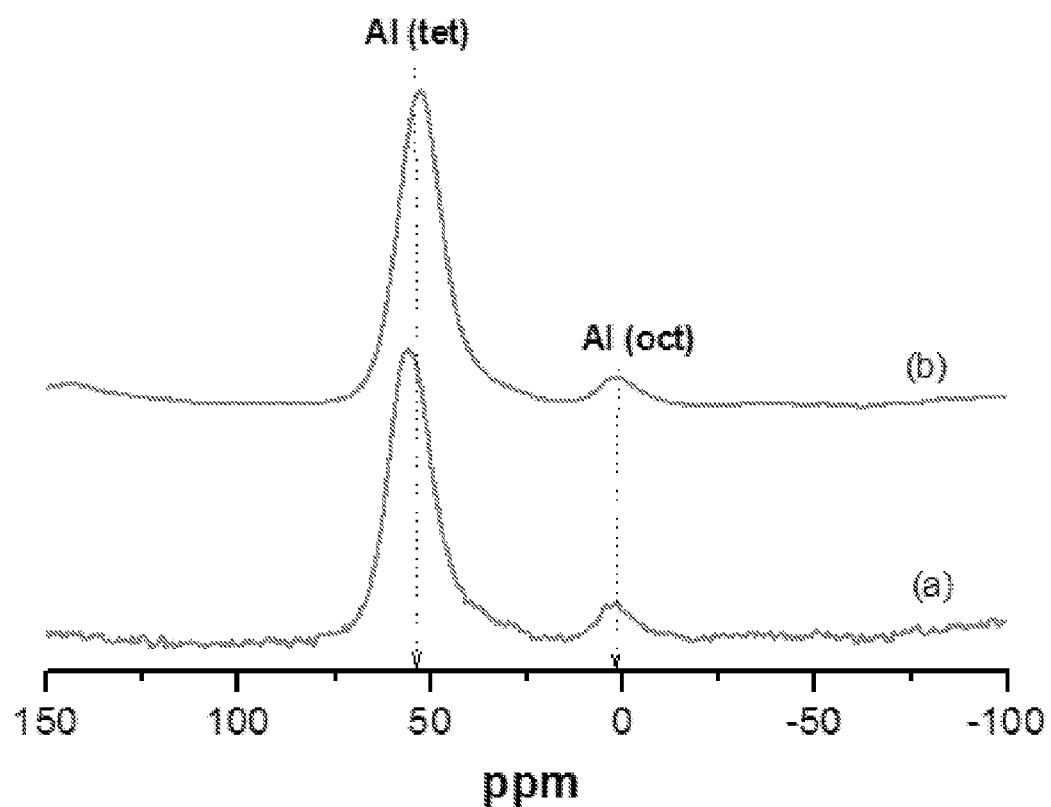
FIG. 3A depicts solid-state $^{27}$Al MAS NMR spectra of (a) silica-alumina and (b) an amine catalyst supported on silica-alumina.
Figure 3B:
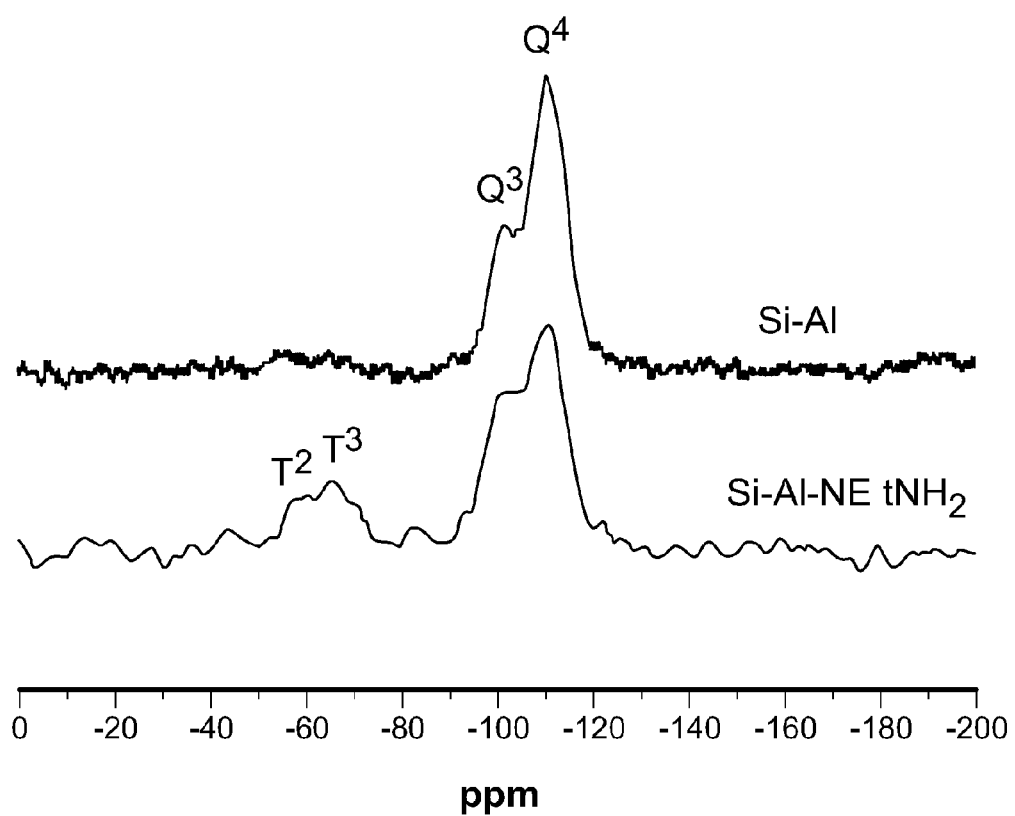
FIG. 3B depicts solid-state $^{29}$Si MAS NMR spectra of silica-alumina and an amine catalyst supported on silica-alumina.

Solid-state $^{13}C$ magic-angle spinning (MAS) NMR confirmed the successful grafting of the respective organosilanes on the Si—Al surfaces. FIG. 2 depicts the solid-state $^{13}C$ MAS NMR spectra of some of the alumina-supported amine catalysts prepared according to the procedure set forth above. The observed chemical shifts of the organic groups agree well with those of the corresponding organosilane precursors measured in solution. $^{29}Si$ MAS NMR further confirmed the presence of organic functional groups grafted on the Si—Al support. FIG. 3B depicts the $^{29}Si$ MAS NMR spectra of some of the alumina-supported amine catalysts prepared according to the procedure set forth above. Peaks at δ=−110, −100, −90, −65, and −55 ppm were assigned to $Q^4(Si(OSi)_4)$, $Q^3(Si(OH)(OSi)_3)$, $Q^2(Si(OH)_2(OSi)_2)$, $T^3(SiR(OSi)_3)$, and $T^2(Si(OH)R(OSi)_2)$ sites, respectively. Presence of peaks at −65 and −55 ppm indicate the formation of T″ sites [$RSi(OEt)_n(OSi)_{3-n}$] and a higher $T^3/T^2$ ratio from the $^{29}Si$ MAS NMR confirms a strong covalent linkage between the organocatalysts and the Si—Al support. FIG. 3A depicts the $^{27}Al$ MAS NMR spectra of some of the alumina-supported amine catalysts prepared according to the procedure set forth above.

Example 2

ABE Reaction Using Si—Al Amine and Al—Pd Catalyst Mixture

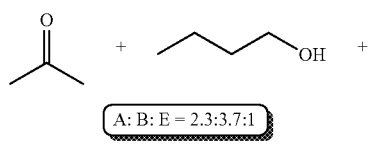

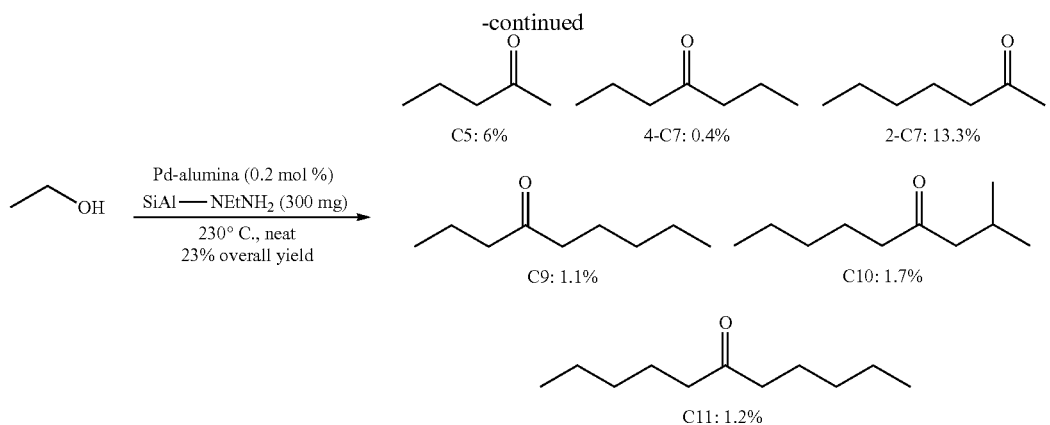

This Example demonstrates the production of a mixture of alkanones from an acetone-butanol-ethanol (ABE) starting mixture using a silica-alumina supported amine catalyst in the presence of an alumina-Pd catalyst.

Preparation of Si—Al Amine Catalyst: The silica-alumina supported diamine catalyst Entry 4 (Si—Al-NEt-NH$_2$) in Table 2 was prepared according to the procedure set forth in Example 1.

Preparation of Alumina-Pd Catalyst: 2.5 wt % Pd on Al$_2$O$_3$ was synthesized by an incipient impregnation method. Specifically 0.075 g of Pd(acac)$_2$ dissolved in ~1 mL of toluene was slowly added to 1 g of Al$_2$O$_3$ support, stirred thoroughly, and dried in a vacuum oven at 373 K for 12 h. The dried sample was then calcined in air at 823 K for 5 h at a heating rate of 5 K/min from room temperature and then reduced in H$_2$ at 823 K for 3 h to obtain the Pd/Al$_2$O$_3$ catalyst.

Reaction Studies: In a 12 mL Q-tube containing a stir bar, 300 mg of silica-alumina supported amine catalyst (Entry 4 in Table 2) and 100 mg 0.2 mol % Pd-alumina was charged to the reaction vessel. To the reaction mixture, 2.3 mmol acetone, 3.7 mmol butanol, and 1 mmol ethanol were sequentially added to the reaction vessel. The Q-tube was sealed and the reaction mixture was stirred for 24 h at 503 K in a pre-heated metal block. The reaction mixture was cooled to room temperature and dodecane (internal standard) was added. The reaction mixture was diluted with tetrahydrofuran and gas chromatography (GC) analysis of the reaction mixture was carried out.

Example 3

$^{13}$C CP MAS NMR Study of Supported and Adsorbed Amine Catalysts

This Example demonstrates the differences between the $^{13}$C CP MAS NMR spectra of an amine catalyst supported by Si—Al or silica, and an amine catalyst adsorbed onto Si—Al or silica.

Figure 4A:
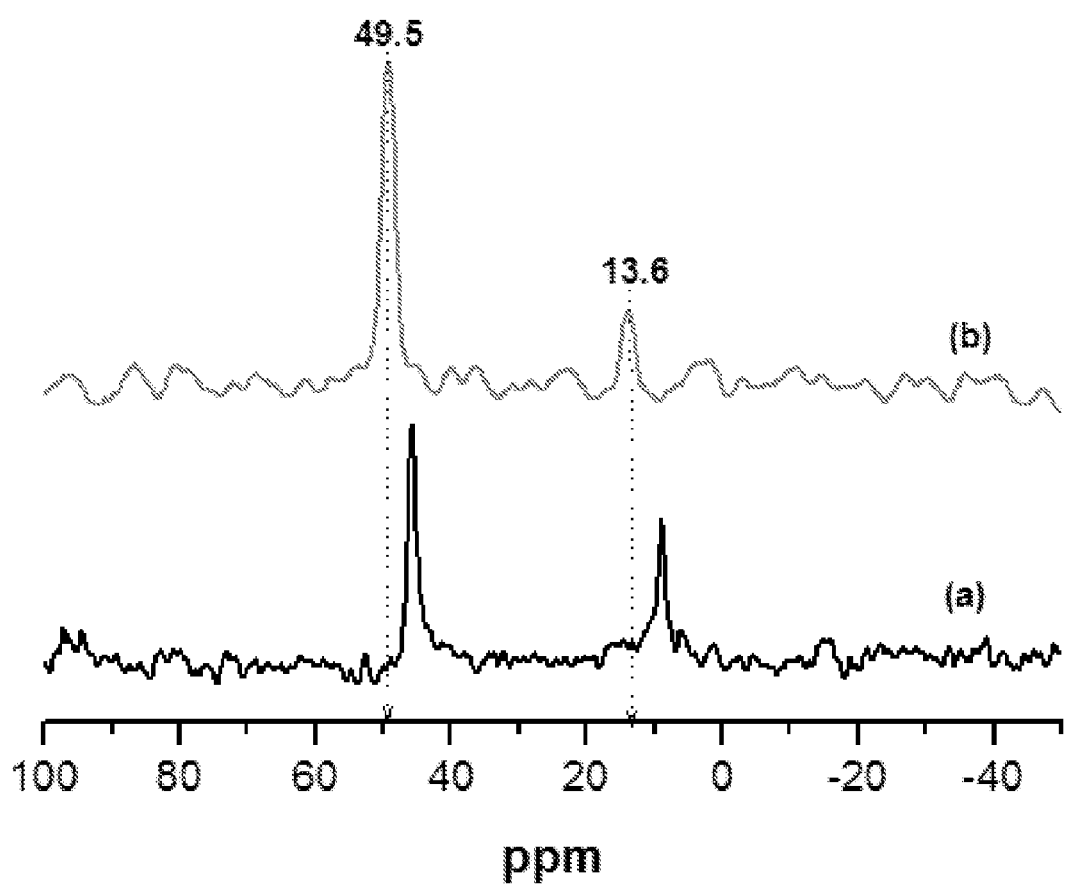
FIG. 4A depicts solid-state $^{13}$C CP MAS NMR spectra of NEt$_3$ adsorbed on (a) silica-alumina and (b) silicon dioxide.
Figure 4B:
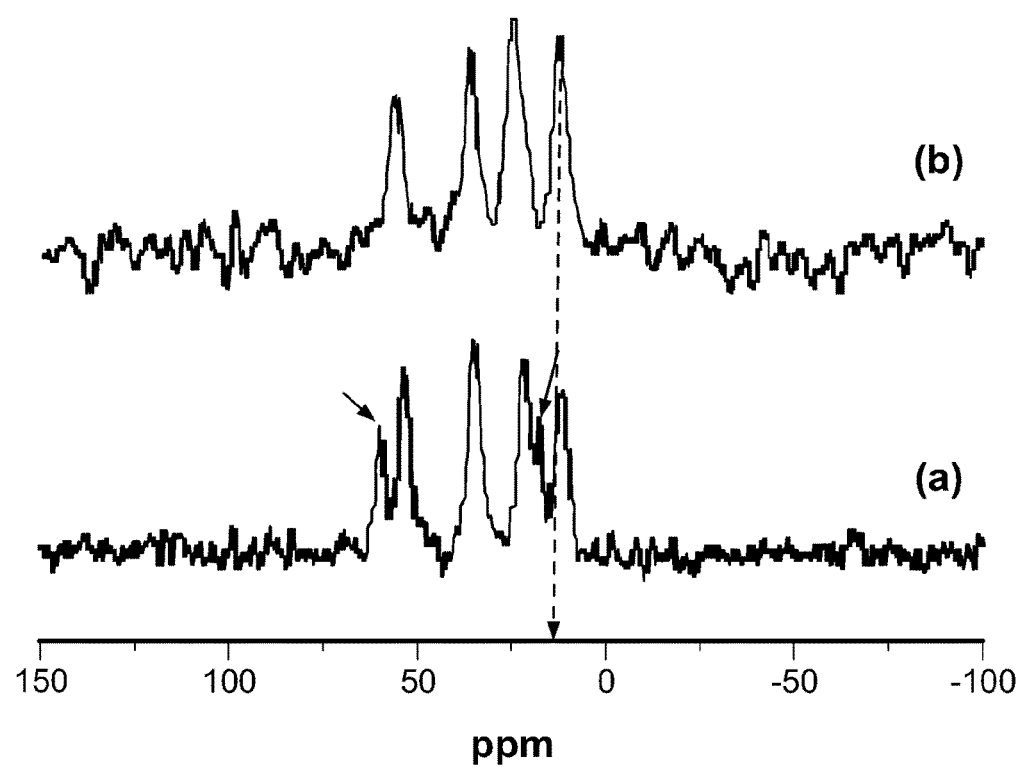
FIG. 4B depicts solid-state $^{13}$C CP MAS NMR spectra of an amine catalyst supported on (a) silica-alumina and (b) silicon dioxide. The two arrows in spectrum (a) refer to the ethoxy peaks obtained by refluxing the Si—Al sample in a solution including ethanol.

The Si—Al supported catalyst used was Si—Al—NHR, as listed in Table 1, prepared as described in Experiment 1. The silica (SiO$_2$) supported catalyst used was SiO$_2$—NHR, prepared in as described in Experiment 1 using silica instead of silica-alumina as the solid support. The adsorbed amine catalysts used were triethylamine adsorbed on Si—Al or SiO$_2$, and were prepared by an impregnation procedure. The $^{13}$C CP MAS NMR spectra of the supported amine catalysts is shown in FIG. 4A. The $^{13}$C CP MAS NMR spectra of the adsorbed amine catalysts is shown in FIG. 4B.

The $^{13}$C CP MAS NMR spectra of triethylamine adsorbed onto Si—Al showed a strong upfield shift in the terminal carbon position, compared to triethylamine adsorbed onto SiO$_2$. The $^{13}$C CP MAS NMR spectra of the Si—Al—NHR sample showed similar peak positions to that in SiO$_2$—NHR, indicating the absence of strong interaction between the Brønsted acid sites and the supported amine groups.

Example 4

Effect of Water on ABE Reaction as Catalyzed by a Supported Amine Catalyst Compared to a Pd-Alumina Catalyst This Example demonstrates the effect of water on the condensation of an ABE mixture to produce longer-chain ketones using a supported amine catalyst as compared to a Pd-alumina catalyst.

Pd-Alumina Catalyst Preparation: The Pd-alumina catalyst is prepared according to the procedure set forth in Example 2.

Supported Amine Catalyst Preparation: The Si—Al supported catalyst used is Si—Al-Proline, as listed in Table 1, prepared according to the procedure set forth in Example 1.

Reaction Studies: The reactions is carried out using a 12 mL Q-tube containing a stir bar. The reaction vessel is charged with 900 mg of silica-alumina supported amine catalyst and 300 mg of 0.2 mol % Pd-alumina. To the reaction vessel is added 2.3 mmol acetone, 3.7 mmol butanol, and 1 mmol ethanol. Water is included in the reaction at different weight percentages of water with respect to the total weight of acetone-butanol-ethanol (ABE) used. The reaction vessel is sealed and the reaction mixture is stirred for 24 h at 503 K in a pre-heated metal block. The reaction mixture is analyzed by gas chromatography.

What claimed is:

1. A method of producing a ketone mixture, comprising contacting a methyl ketone and at least one alcohol with an amine catalyst and a metal catalyst to produce a ketone mixture from the condensation of the methyl ketone and the at least one alcohol, wherein:

the methyl ketone has the structure of Formula (A):

(A)

wherein:
R¹ is H, alkyl, carbocyclyl, or heterocyclyl;
wherein the alkyl, carbocyclyl, or heterocyclyl is unsubstituted or substituted with one or more substituents independently selected from the group consisting of hydroxyl, nitro, and halo; and
x is an integer greater than or equal to 1; and
the amine catalyst comprises an amine moiety, a solid support, and a linker, wherein the linker attaches the amine moiety to the solid support.

2. The method of claim 1, wherein the methyl ketone and the at least one alcohol are contacted with the amine catalyst and the metal catalyst in the presence of water.

3. The method of claim 1, further comprising contacting a composition comprising biomass or sugars with a fermentation host to produce a fermentation product mixture, wherein the fermentation product mixture comprises at least a portion of the methyl ketone and the at least one alcohol.

4. A method of producing a ketone mixture, comprising:
contacting a composition comprising biomass or sugars with a fermentation host to produce a fermentation product mixture, wherein the fermentation product mixture comprises acetone, butanol and ethanol; and
contacting the acetone, butanol and ethanol with an amine catalyst and a metal catalyst to produce a ketone mixture, wherein:
the amine catalyst comprises an amine moiety, a solid support, and a linker, wherein the linker attaches the amine moiety to the solid support.

5. The method of claim 4, wherein at least a portion of the ketone mixture produced is by double alkylation of the acetone.

6. The method of claim 1, wherein at least 15% of the ketone mixture produced is $C_{7+}$ hydrocarbon ketones.

7. The method of claim 1, wherein at least 25% of the ketone mixture produced is $C_{5+}$ hydrocarbon ketones.

8. The method of claim 1, wherein the amine moiety has the structure:

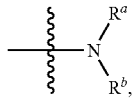

wherein $R^a$ and $R^b$ at each occurrence are independently H, alkyl, carbocyclyl, heterocyclyl, or ether, or any combinations thereof;
wherein the alkyl, carbocyclyl, heterocyclyl, or ether is independently unsubstituted or substituted with one or more substituents selected from the group consisting of alkyl, hydroxyl, amine, oxo, carboxyl, imine, carbocyclyl, heterocyclyl, halo, ether, and thioether;
or $R^a$ and $R^b$ are taken together with the nitrogen atom to which they are both attached to form a heterocycle,
wherein the heterocycle is unsubstituted or substituted with one or more substituents selected from the group consisting of alkyl, hydroxyl, amine, oxo, carboxyl, imine, carbocyclyl, heterocyclyl, halo, ether, and thioether.

9. The method of claim 1, wherein the amine moiety comprises a heterocycle containing at least one nitrogen atom, wherein the heterocycle is unsubstituted or substituted with one or more substituents selected from the group consisting of alkyl, carbocyclyl, heterocyclyl, carboxyl, hydroxyl, halo, ether, and thioether.

10. The method of claim 1, wherein the solid support comprises silica, alumina, silica-alumina, $TiO_2$, $ZrO_2$, or $Nb_2O_5$, or any combinations thereof.

11. The method of claim 1, wherein the solid support is porous.

12. The method of claim 1, wherein the solid support comprises a plurality of pores, wherein at least a portion of the pores have a pore diameter between 2 nm and 50 nm.

13. The method of claim 1, wherein the solid support comprises an acid moiety.

14. The method of claim 1, wherein the linker comprises:
-alkyl-, -aliphatic-, -aryl-, -carbocycle-, -heterocycle-, -sulfone-, or -ether-, or any combinations thereof;
wherein the -alkyl-, -aliphatic-, -aryl-, -carbocycle-, -heterocycle-, -sulfone-, -ether- are unsubstituted or substituted with one or more substituents independently selected from the group consisting of alkyl, hydroxyl, amine, oxo, carboxyl, imine, carbocyclyl, and heterocyclyl.

15. The method of claim 1, wherein the linker comprises at least three linear chain atoms.

16. The method of claim 1, wherein the amine catalyst comprises a secondary amine.

17. The method of claim 1, wherein the metal catalyst is palladium on alumina.

18. A composition, comprising:
a methyl ketone of Formula (A):

wherein:
R¹ is H, alkyl, carbocyclyl, or heterocyclyl;
wherein the alkyl, carbocyclyl, or heterocyclyl is unsubstituted or substituted with one or more substituents independently selected from the group consisting of hydroxyl, nitro, and halo; and
x is an integer greater than or equal to 1;
at least one alcohol;
an amine catalyst, wherein the amine catalyst comprises an amine moiety, a solid support, and a linker, wherein the linker attaches the amine moiety to the solid support; and
a metal catalyst.

19. The composition of claim 18, further comprising water.

20. The composition of claim 18, wherein the amine moiety has-the structure:

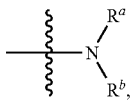

wherein $R^a$ and $R^b$ at each occurrence are independently H, alkyl, carbocyclyl, heterocyclyl, or ether, or any combinations thereof;

wherein the alkyl, carbocyclyl, heterocyclyl, or ether is independently unsubstituted or substituted with one or more substituents selected from the group consisting of alkyl, hydroxyl, amine, oxo, carboxyl, imine, carbocyclyl, heterocyclyl, halo, ether, and thioether;

or $R^a$ and $R^b$ are taken together with the nitrogen atom to which they are both attached to form a heterocycle, wherein the heterocycle is unsubstituted or substituted with one or more substituents selected from the group consisting of alkyl, hydroxyl, amine, oxo, carboxyl, imine, carbocyclyl, heterocyclyl, halo, ether, and thioether.

21. The composition of claim 18, wherein the amine moiety comprises a heterocycle containing at least one nitrogen atom, wherein the heterocycle is unsubstituted or substituted with one or more substituents selected from the group consisting of alkyl, carbocyclyl, heterocyclyl, carboxyl, hydroxyl, halo, ether, and thioether.

22. A composition, comprising:
a fermentation product mixture comprising a methyl ketone, at least one alcohol;
an amine catalyst, wherein the amine catalyst comprises an amine moiety, a solid support, and a linker, wherein the linker attaches the amine moiety to the solid support;
a metal catalyst; and
water.

23. A method, comprising:
producing a ketone mixture according to the method of claim 1; and
hydrodeoxygenating at least a portion of the ketone mixture to produce an alkane or a mixture of alkanes.

24. A method, comprising:
producing a ketone mixture according to the method of claim 1; and
reducing at least a portion of the ketone mixture to produce an alcohol or a mixture of alcohols.

* * * * *